US 6,686,490 B1

(12) United States Patent
Kol et al.

(10) Patent No.: US 6,686,490 B1
(45) Date of Patent: Feb. 3, 2004

(54) ACTIVE NON-METALLOCENE PRE-CATALYST AND METHOD FOR TACTIC CATALYTIC POLYMERIZATION OF ALPHA-OLEFIN MONOMERS

(75) Inventors: Moshe Kol, Ramat Gan (IL); Edit Y. Tshuva, Rehovot (IL)

(73) Assignee: Ramot University Authority for Applied Research & Industrial Development Ltd., Tel Aviv (IL)

( * ) Notice: Subject to any disclaimer, the term of this patent is extended or adjusted under 35 U.S.C. 154(b) by 0 days.

(21) Appl. No.: 09/705,780

(22) Filed: Nov. 6, 2000

(51) Int. Cl.$^7$ ............................... C07F 7/00; C07F 7/28

(52) U.S. Cl. .................. 556/56; 502/155; 526/161; 526/171

(58) Field of Search ................... 556/56; 502/155; 526/161, 171

(56) References Cited

U.S. PATENT DOCUMENTS 5,707,913 A * 1/1998 Schlund et al. ............. 502/102
5,852,146 A   12/1998 Reichle et al. ............. 526/172
5,889,128 A * 3/1999 Schrock et al. ............. 526/107

OTHER PUBLICATIONS

Eisen et al., Organometallics, 1998, 17, 3155–3157.*
Eisen et al., J. Am. Chem. Soc. 1998, 120 8640–8646.*
Schweder et al., JOMC 508 (1996) 13–22.*
Eisen et al., JOMC 503 (1995) 307–314.*

(List continued on next page.)

Primary Examiner—David W. Wu
Assistant Examiner—R. Harlan
(74) Attorney, Agent, or Firm—G. E. Ehrlich Ltd.

(57) ABSTRACT

An active non-metallocene pre-catalyst featuring a diamine diphenolate complex and a corresponding method for catalytic polymerization, in general, and, tactic catalytic polymerization, in particular, of alpha-olefin monomers using the disclosed pre-catalyst. General formulas of the non-metallocene diamine diphenolate pre-catalyst are $[\{OR^5R^6R^7R^8(C_6)^1(CHR^3)NR^1YNR^2(CHR^4)(C_6)^2R^9R^{10}R^{11}R^{12}O\}MX^1X]$ and $[\{OR^5R^6R^7R^8(C_6)^1(CHR^3)NR^1YNR^2(CHR^4)(C_6)^2R^9R^{10}R^{11}R^{12}O\}MX^3]$, where M is a metal atom covalently bonded to each oxygen atom, O, and, bonded to each nitrogen atom, N, with varying degrees of covalency and coordination; $X^1$ and $X^2$ are each a univalent anionic ligand covalently bonded to the metal atom; $X^3$ is a single univalent or a divalent anionic ligand covalently bonded to the metal atom; $R^1$ and $R^2$ are each a univalent radical covalently bonded to a different one of the two nitrogen atoms; $R^3$ is a univalent radical covalently bonded to the carbon atom of the —$CHR^3$— of the $(C_6)^1$—$CHR^3$—N— bridging unit; $R^4$ is a univalent radical covalently bonded to the carbon atom of the —$CHR^4$— of the —N—$CHR^4$—$(C_6)^2$ bridging unit; $R^5$ through $R^8$ are each a univalent radical covalently bonded to a different carbon atom in the first aromatic group, $(C_6)^1$; $R^9$ through $R^{12}$ are each a univalent radical covalently bonded to a different carbon atom in the second aromatic group, $(C_6)^2$; and, Y is a divalent radical covalently bonded to and bridging between the two nitrogen atoms. The diamine diphenolate pre-catalyst, when activated by a co-catalyst under mild reaction conditions, is active for isotactic (isospecific) and living polymerization of a variety of alpha-olefin monomers, such as 1-hexene, for forming poly(alpha-olefin) products, such as poly(1-hexene), having classifiable degree of tacticity, high molecular weight and low molecular weight distribution.

38 Claims, 4 Drawing Sheets

OTHER PUBLICATIONS van der Linden et al, "Polymerization of α–Olefins and Butadiene and Catalytic Cyclotrimerization of 1–Alkynes by a New Class of Group IV Catalysts. Control of Molecular Weight and Polymer Microstructure via Ligan Tuning in Sterically Hindered Chelating Phenoxide Titanium and Zirconium Species", *J. Am. Chem. Soc.*, 117:3008–3021, 1995.

Scollard et al, "Living Polymerization of α–Olefins by Chelating Diamide Complexes of Titanium", *J. Am. Chem. Soc.*, 118:10008–10009, 1996.

Jeon et al, "Zirconium Complexes with the New Ancillary Diamido Ligand 2,2'–Ethylenebis (N,N–(triisopropylsilyl)anilinido)$^{2-}$: Syntheses, Structures, and Living α–Olefin Polymerization Activities", *Organometallics*, 17:3161–3163, 1998.

* cited by examiner

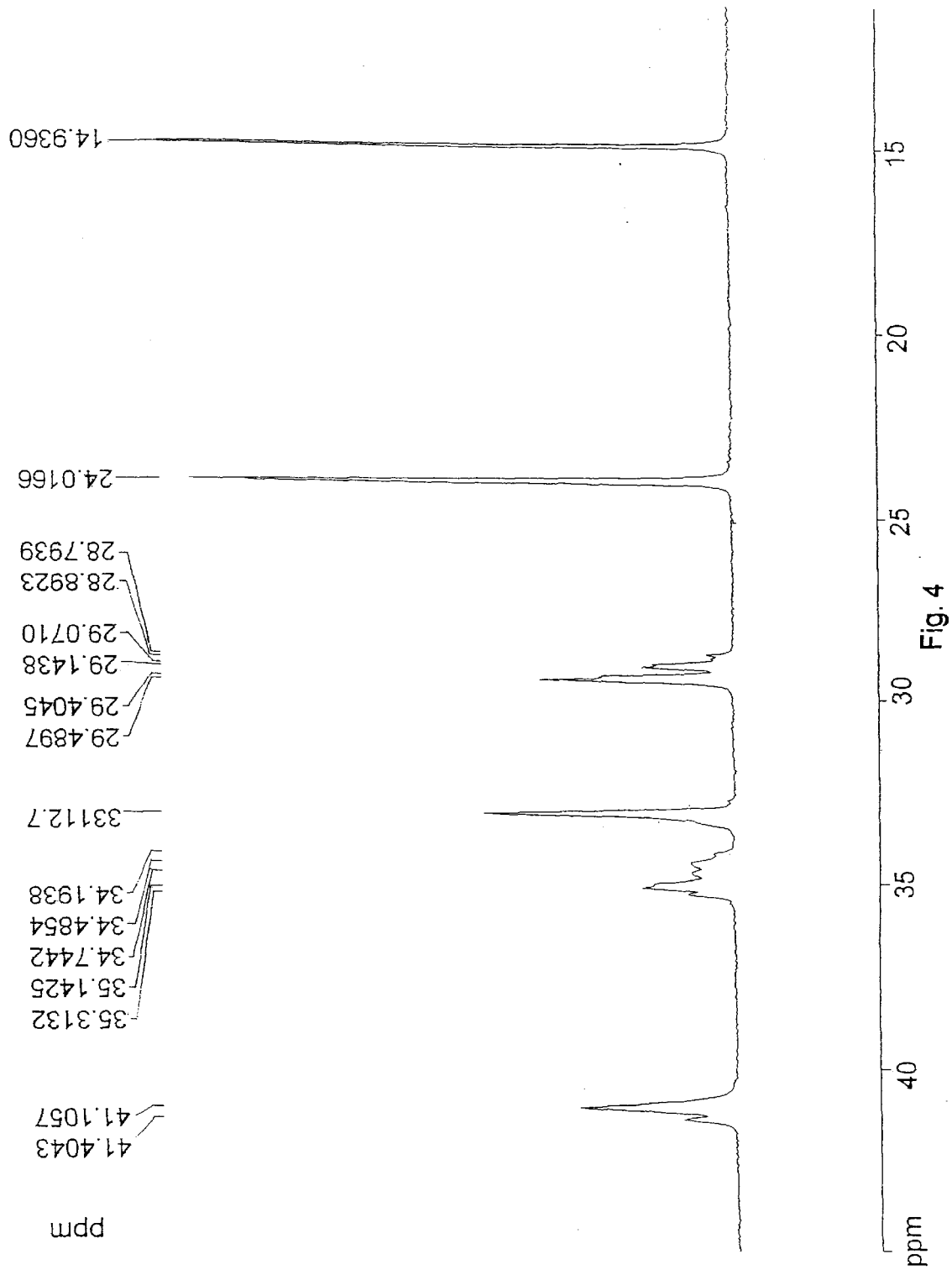

ACTIVE NON-METALLOCENE PRE-CATALYST AND METHOD FOR TACTIC CATALYTIC POLYMERIZATION OF ALPHA-OLEFIN MONOMERS

FIELD AND BACKGROUND OF THE INVENTION

The present invention relates to catalytic polymerization, in general, and, tactic catalytic polymerization, in particular, of alpha-olefin monomers using an active non-metallocene pre-catalyst featuring a diamine diphenolate complex, and a corresponding method using the disclosed pre-catalyst.

Currently, there is significant interest relating to methods and systems of catalytic polymerization of alpha-olefin monomers based on a 'pre-catalyst' featuring a metal bound to one or more spectator ligands, where the pre-catalyst may be soluble in a liquid phase solvent, or is adsorbed on a solid surface, and where alpha-olefin monomer reactant may be liquid or gas phase. In such methods and systems, typically, the pre-catalyst is activated by at least one 'co-catalyst', where the combination of the activated pre-catalyst and the at least one co-catalyst functions as a single chemical entity, or complex 'catalyst', for polymerization of the alpha-olefin monomer. The field of catalytic polymerization of alpha-olefin monomers is of significant industrial importance, as more than 50 million tons of poly(alpha-olefin) products, such as polyetheylenes and polypropylenes, are produced each year, involving metal based catalytic processes and systems.

Hereinafter, the term 'pre-catalyst' refers to a chemical entity, in general, and to a chemical compound, in particular, which, when activated by at least one 'co-catalyst', becomes part of a 'catalyst' functional for catalytic polymerization of an alpha-olefin monomer, under proper polymerization reaction conditions. In general, without the presence of at least one co-catalyst, a pre-catalyst is ineffective for catalytic polymerization of an alpha-olefin monomer, and consequently exhibits essentially no catalytic activity for polymerization of an alpha-olefin monomer. Here, when referring to catalytic activity during a polymerization reaction, reference is with respect to the catalytic activity of a pre-catalyst, and it is to be understood that the pre-catalyst functions in concert with at least one co-catalyst for effecting catalytic polymerization of an alpha-olefin monomer. It is noted, however, that there are rare exceptions of a particular pre-catalyst functioning without first being activated by a co-catalyst, for effecting catalytic polymerization of an alpha-olefin monomer. Thus, the present invention focuses on a new and novel pre-catalyst compared to pre-catalysts currently used for catalytic polymerization of alpha-olefin monomers.

Currently, one of the major goals in this field is to produce a variety of new types of poly(alpha-olefin) products, for example, tactic polymers made from alpha-olefin monomers featuring more than two carbon atoms, having well defined bulk or global physicochemical properties, such as mechanical strength, elasticity, melting point, and chemical resistance, applicable for manufacturing a diversity of end products. This may be achieved by controlling the polymer tacticity and polymerizing different types of alpha-olefin monomers, in order to produce a variety of homo-polymers and co-polymers, with varying degrees of monomer incorporation.

Bulk or global physicochemical properties of polymers are directly related to, and are controllable by, molecular or local physicochemical characteristics of the polymer units making up the bulk polymer. Three notable molecular physicochemical characteristics are polymer molecular weight, polymer molecular weight distribution, and polymer tacticity.

Polymer molecular weight and polymer molecular weight distribution are highly relevant with respect to producing different types of polymers. For example, ultra-high molecular weight polyethylene (UHMWPE), having an average molecular weight above 3,000,000, has the highest abrasion resistance of thermoplastics and a low coefficient of friction. Unlike synthesis of small molecules, however, polymerization reactions involve random events characterized by formation of polymer chains having a range of molecular weights, rather than a single molecular weight. Typically, polymers are better defined and characterized in relation to narrow molecular weight ranges.

The accepted parameter for defining polymer molecular weight distribution is the polydispersity index (PDI), which is the weight average molecular weight, $M_w$, divided by the number average molecular weight, $M_n$, or, $M_w/M_n$. Depending upon the actual application, ideally, a catalytic polymerization system features 'living' polymerization in which the rate of initiation is higher than the rate of propagation leading to a PDI of close to 1, and involving a single catalytic active site, and the rate of termination reactions is negligible relative to propagation. This has been achieved in very few systems for catalytic polymerization of alpha-olefin monomers. A PDI of 2.0, signifying 'non-living' polymerization, is often found in metallocene catalytic systems, also involving a single catalytic active site. Classical heterogeneous Ziegler-Natta catalytic systems usually lead to a broader range of molecular weights with a PDI of about 5. One current challenge is to design alpha-olefin polymerization pre-catalysts, and catalytic systems including such pre-catalysts, leading to poly(alpha-olefin) products with low values of PDI.

Another current challenge in the field of catalytic polymerization of alpha-olefins is to design alpha-olefin polymerization pre-catalysts, and catalytic systems including such pre-catalysts, leading to poly(alpha-olefin) products having controllable and classifiable degrees of polymer tacticity. Polymer tacticity is another very significant molecular physicochemical characteristic of a polymer which can dramatically determine and influence bulk physicochemical properties of a polymer, such as a poly(alpha-olefin) polymer. The term 'polymer tacticity' refers to the particular micro- or local structural configuration of the substituents on the polymer backbone, or equivalently, stereo-regularity of the polymer chain, as to whether a polymer is, for example, isotactic, syndiotactic, or, atactic. Polymer tacticity is typically used in reference to a hydrocarbon polymer derived from polymerization of a monomer having more than two carbon atoms, such that the polymer has a side chain on every other carbon atom of the polymer backbone. Moreover, there are different particular forms or types of 'polymer tacticity' according to the particular micro- or local structure in terms of the relative orientations of the side chains bound to the polymer backbone.

A polymer in which all the side chains extend or protrude from the same side or plane of the polymer backbone is referred to as an 'isotactic polymer' which is obtained from an 'isotactic', or equivalently, an 'isospecific' polymerization process. A polymer in which the side chains alternately extend or protrude from opposite sides of the polymer backbone is referred to as a 'syndiotactic polymer' which is obtained from a 'syndiotactic', or equivalently, a 'syndiospecific' polymerization process. A polymer in which the side chains randomly extend or protrude from either side of the polymer backbone is referred to as an 'atactic polymer', which is obtained from an 'atactic' polymerization process. Furthermore, extent or degree of a particular form or type of polymer tacticity is also used in reference to polymer tacticity. For example, a polymer may be classified as being eighty percent isotactic and twenty percent atactic. Another example is a hemi-isotactic polymer, in which every second side chain extends or protrudes from the same side or plane of the polymer backbone, whereas the rest of the side chains randomly extend or protrude from either side of the polymer backbone. Typically, extent or degree of tacticity of a polymer, or a polymerization process, is determined by subjecting the polymer, or products of the polymerization process, to NMR spectroscopic analysis, more particularly, $^{13}$C NMR.

An illustrative example showing the dramatic influence polymer tacticity has on bulk physicochemical properties of a polymer is tactic polymerization of propylene. Isotactic polypropylene is solid and semi-transparent at room temperature with a melting point in the range 150–165° C., syndiotactic polypropylene is a transparent solid at room temperature with a melting point of about 145° C., and atactic polypropylene is a viscous oil at room temperature.

Metallocene pre-catalysts, featuring a metal complex including a metal atom, for example from Group IV transition elements such as titanium, zirconium, and hafnium, bound to two ligands from the well known cyclopentadienyl (Cp) family of ligands such as pentamethylcyclopentadienyl, indenyl, or fluorenyl, were introduced during the last two decades for the purpose of catalytic polymerization of alpha-olefin monomers. The most common type of metallocene pre-catalyst is a neutral complex including a metal in oxidation state of +4, bound to two anionic ligands in addition to two standard Cp ligands, for example, bis(cyclopentadienyl)titanium dichloride, also known as titanocene dichloride. A particular group of metallocene pre-catalysts is known as ansa-metallocene complexes, in which the two Cp type ligands are covalently bonded to each other. A related group of complexes is 'constrained geometry' pre-catalysts, featuring a metal bound to both a single Cp type ligand and a second anionic group, where the Cp ligand and second anionic group are covalently bonded to each other.

Using metallocene and metallocene type pre-catalysts in catalytic processes and systems for polymerization of alpha-olefin monomers affords better control of molecular weight and narrower molecular weight distribution, associated with lower values of PDI, relative to the classical Ziegler-Natta family of pre-catalysts such as titanium trichloride using a trialkyl-aluminum co-catalyst. Moreover, the group of ansa-metallocene pre-catalysts is useful for producing polymers with controllable and classifiable degrees of polymer tacticity. Metallocene and metallocene type pre-catalysts, processes, and systems are well known and taught about in the art. These pre-catalysts, processes and systems are, however, limited in many respects relating to the above discussion.

Foremost, with respect to catalytic activity, metallocene type pre-catalysts typically exhibit relatively moderate activity for polymerizing a small variety of alpha-olefin monomers. With respect to poly(alpha-olefin) product types and variety, alpha-olefin monomers polymerized by metallocene pre-catalysts are mostly short chain ethylene and propylene, which are already well taught about. Metallocene pre-catalysts are limited in terms of availability and versatility. Metallocene type pre-catalysts are relatively difficult to synthesize, a fact which limits the possibility of developing new varieties of metallocene type alpha-olefin polymerization pre-catalysts.

Due to continued searching for new poly(alpha-olefin) products exhibiting selected well defined bulk physicochemical properties and molecular physicochemical characteristics, combined with the above limitations associated with metallocene pre-catalysts, there is growing interest in developing non-metallocene alpha-olefin polymerization pre-catalysts, and related catalytic processes, and systems. The main emphasis is on obtaining new alpha-olefin polymerization pre-catalysts which are readily available, exhibit relatively high stability, and can be used for improving control over industrially important polymer parameters such as molecular weight, molecular weight distribution, product types and variety, and, controllable and classifiable polymer tacticity.

The principle of controlling polymer tacticity by ligands design was first demonstrated for various catalytic systems featuring the group of ansa-metallocene complex pre-catalysts, as reviewed by Brintzinger, H. H. et. al. in Angew. Chem., Int. Ed. Engl. 34, 1143, 1995. Catalytic systems described therein usually lead to a PDI not less than 2.0, and suffer from the above described disadvantages and limitations of metallocene systems.

An example of a 'half sandwich' pre-catalyst, featuring a complex including one Cp type ligand and a heteroatom donor, is described by Sita, L. R., in J. Am. Chem. Soc. 122, 958, 2000. This half metallocene catalytic system is active with regard to polymer isospecificity and living polymerization of alpha olefin monomers. However, this system involves operating at commercially undesirable reaction conditions, such as at −10 degrees Celsius.

A non-metallocene alpha-olefin polymerization catalytic system is disclosed in U.S. Pat. No. 5,852,146, and features a bis(hydroxy aromatic nitrogen ligand) transition metal pre-catalyst, functioning with an activating methylaluminoxane (MAO) co-catalyst. Relatively high catalytic activity of about 4,000 grams/(mmole-pre-cat. hr) is reported for polymerization of ethylene only. Moreover, MAO is needed in large quantities as co-catalyst, which, in general, poses notable limitations relating to cost and containment. MAO used in large quantities is costly, and needs to be properly disposed of with regard to environmental considerations.

Living polymerization of 1-hexene is described by Schrock, R. R., in J. Am. Chem. Soc. 119, 3830, 1997, and is disclosed in U.S. Pat. No. 5,889,128. One of the non-metallocene pre-catalyst compositions described therein comprises a dimethyl complex in which the metal atom is chelated to a tridentate spectator ligand, which is activated by a non-MAO boron salt co-catalyst. However, only atactic polymeric products are obtained from this system.

Living polymerization of 1-hexene is also described by McConville, D. H., in J. Am. Chem. Soc. 118, 10008, 1996. They describe an active non-metallocene polymerization pre-catalyst, involving activation of a pre-catalyst featuring a dimethyl metal complex of a bis(amide) ligand, with a non-MAO boron Lewis acid as co-catalyst under room temperature, for producing atactic polymers.

Another active non-metallocene living 1-hexene polymerization pre-catalyst functioning with a non-MAO co-catalyst, is reported by Kim, K., in Organometallics 17, 3161, 1998. Similar to other teachings, the described catalytic system yields only atactic polymers.

A non-metallocene diphenolate pre-catalyst is reported by Schaverien, C. J., in J. Am. Chem. Soc. 117, 3008, 1995. Use of the disclosed pre-catalyst leads to highly isotactic poly (1-hexene), however, the polymerization process is not living.

Recently, the present inventors, in U.S. patent application Ser. No. 09/394,280, filed Sep. 20, 1999, disclosed of an ultra-high activity non-metallocene pre-catalyst featuring an amine diphenolate complex and a corresponding method for catalytic polymerization of alpha-olefin monomers using this pre-catalyst. However, only atactic polymers are obtained using the disclosed pre-catalyst at the indicated polymerization conditions.

In view of the above discussed limitations for polymerization of alpha-olefins, to one of ordinary skill in the art, there is thus a need for, and it would be highly advantageous to have an active non-metallocene pre-catalyst and corresponding method for catalytic polymerization of alpha-olefin monomers, not limited to activation by large quantities of a co-catalyst such as MAO, and also characterized by high stability, readily obtained or synthesized, and capable of producing different types and varieties of poly(alpha-olefin) products having high molecular weight and low molecular weight distribution, and, controllable and classifiable degrees of polymer tacticity. Moreover, there is a need of such a pre-catalyst and methods for producing alpha-olefin polymers other than polyethylenes and polypropylenes, having industrially applicable properties and characteristics.

SUMMARY OF THE INVENTION

The present invention relates to catalytic polymerization, in general, and, tactic catalytic polymerization, in particular, of alpha-olefin monomers using an active non-metallocene pre-catalyst featuring a diamine diphenolate complex. Moreover, the present invention features a general method for catalytic polymerization, including a particular method for tactic catalytic polymerization, of alpha-olefin monomers, using the disclosed diamine diphenolate pre-catalyst.

It is therefore an object of the present invention to provide general structures and general formulas of an active non-metallocene pre-catalyst for catalytic polymerization, in general, and tactic catalytic polymerization, in particular, of alpha-olefin monomers.

It is a further object of the present invention to provide general structures and general formulas of an active non-metallocene pre-catalyst for catalytic polymerization, in general, and tactic catalytic polymerization, in particular, of alpha-olefin monomers, wherein the pre-catalyst is a diamine diphenolate complex featuring variability of the metal atom, ligands, aromatic groups, aromatic group substituents, a bridging group, and bridging group substituents.

It is another object of the present invention to provide a method for catalytic polymerization, in general, and tactic catalytic polymerization, in particular, of alpha-olefin monomers featuring the use of an active diamine diphenolate pre-catalyst, wherein the pre-catalyst features variability of the metal atom, ligands, aromatic groups, aromatic group substituents, a bridging group, and bridging group substituents.

It is another object of the present invention to provide a method for catalytic polymerization, including tactic catalytic polymerization, of alpha-olefin monomers featuring the use of an active diamine diphenolate complex, whereby the polymerization process is essentially a living system.

Thus, according to the present invention, there is provided a compound having a general structure selected from the group consisting of structure 1 and structure 2:

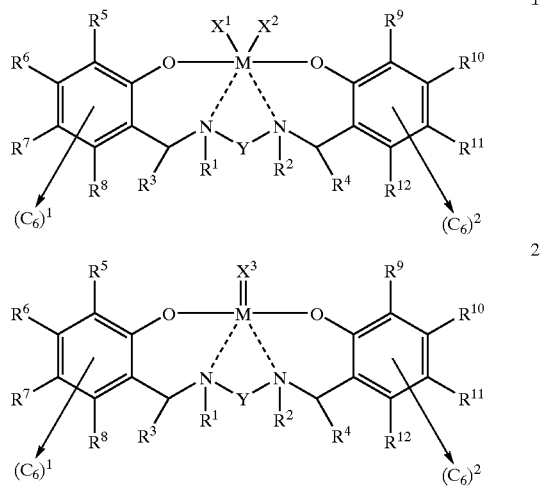

wherein each structure 1 and structure 2: each single solid line represents a covalent bond; each double solid line represents a bond having varying degrees of covalency; each dashed line represents a bond having a varying degree of covalency and a varying degree of coordination; the M is a metal atom covalently bonded to each O oxygen atom, and bonded with varying degrees of covalency and coordination to each N nitrogen atom; the $X^1$ and the $X^2$ are each a univalent anionic ligand covalently bonded to the metal atom; the $X^3$ is a single anionic ligand covalently bonded to the metal atom; the $R^1$ and the $R^2$ are each a univalent radical covalently bonded to a different one of the N nitrogen atoms; the $R^3$ is a univalent radical covalently bonded to the C carbon atom of the —$CHR^3$— of the $(C_6)^1$—$CHR^3$—N— bridging unit; the $R^4$ is a univalent radical covalently bonded to the C carbon atom of the —$CHR^4$— of the —N—$CHR^4$—$(C_6)^2$ bridging unit; each of the $R^5$ through $R^8$ is a univalent radical covalently bonded to a different one of the C carbon atoms of the $(C_6)^1$ first aromatic group; each of the $R^9$ through $R^{12}$ is a univalent radical covalently bonded to a different one of the C carbon atoms of the $(C_6)^2$ second aromatic group; and the Y is a divalent radical covalently bonded to and bridging between both of the N nitrogen atoms.

According to another aspect of the present invention, there is provided a compound of a general formula selected from the group consisting of: [{$OR^5R^6R^7R^8(C_6)^1(CHR^3)NR^1YNR^2(CHR^4)(C_6)^2R^9R^{10}R^{11}R^{12}O$}$MX^1X^2$] and [{$OR^5R^6R^7R^8(C_6)^1(CHR^3)NR^1YNR^2(CHR^4)(C_6)_2R^9R^{10}R^{11}R^{12}O$}$MX^3$], wherein each general formula: the M is a metal atom covalently bonded to each O oxygen atom, and bonded with varying degrees of covalency and coordination to each N nitrogen atom; the $X^1$ and $X^2$ are each a univalent anionic ligand covalently bonded to the metal atom; the $X^3$ is a single anionic ligand covalently bonded to the metal atom; the $R^1$ and $R^2$ are each a univalent radical covalently bonded to a different one of the N nitrogen atoms; the $R^3$ is a univalent radical covalently bonded to the C carbon atom of the —$CHR^3$— of the $(C_6)^1$—$CHR^3$—N— bridging unit; the $R^4$ is a univalent radical covalently bonded to the C carbon atom of the —$CHR^4$— of the —N—$CHR^4$—$(C_6)^2$ bridging unit; each of the $R^5$ through $R^8$ is a univalent radical covalently bonded to a different one of said C carbon atoms of said $(C_6)^1$ first aromatic group; each of the $R^9$ through $R^{12}$ is a univalent radical covalently bonded to a different one of the C carbon atoms of the $(C_6)^2$ second aromatic group; and the Y is a divalent radical covalently bonded to and bridging between both of the N nitrogen atoms.

According to another aspect of the present invention, there is provided a method for catalytic polymerization of an alpha-olefin monomer, the method comprising the steps: (a) providing a diamine diphenolate pre-catalyst having a general structure selected from the group consisting of:

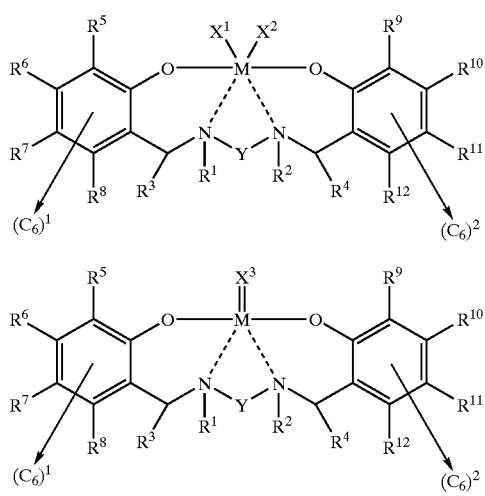

wherein each structure 1 and structure 2: each single solid line represents a covalent bond; each double solid line represents a bond having varying degrees of covalency; each dashed line represents a bond having a varying degree of covalency and a varying degree of coordination; the M is a metal atom covalently bonded to each O oxygen atom, and bonded with varying degrees of covalency and coordination to each N nitrogen atom; the $X^1$ and the $X^2$ are each a univalent anionic ligand covalently bonded to the metal atom; the $X^3$ is a single anionic ligand covalently bonded to the metal atom; the $R^1$ and the $R^2$ are each a univalent radical covalently bonded to a different one of the N nitrogen atoms; the $R^3$ is a univalent radical covalently bonded to the C carbon atom of the —$CHR^3$— of the $(C_6)^1$—$CHR^3$—N— bridging unit; the $R^4$ is a univalent radical covalently bonded to the C carbon atom of the —$CHR^4$— of the —N—$CHR^4$—$(C_6)^2$ bridging unit; each of the $R^5$ through $R^8$ is a univalent radical covalently bonded to a different one of the C carbon atoms of the $(C_6)^1$ first aromatic group; each of the $R^9$ through $R^{12}$ is a univalent radical covalently bonded to a different one of the C carbon atoms of the $(C_6)^2$ second aromatic group; and the Y is a divalent radical covalently bonded to and bridging between both of the N nitrogen atoms; (b) preparing a first chemical entity featuring a particular form of the pre-catalyst of Step (a); (c) providing a co-catalyst suitable for activating the pre-catalyst of Step (a); (d) preparing a second chemical entity featuring the co-catalyst of Step (c); (e) forming a catalytic polymerization reaction system for the catalytic polymerization of the alpha-olefin monomer by mixing the first chemical entity featuring the pre-catalyst with the second chemical entity featuring the co-catalyst with the alpha-olefin monomer to be polymerized, whereby the co-catalyst activates the pre-catalyst for becoming a catalyst effecting the catalytic polymerization of the alpha-olefin monomer for producing at least one type of poly(alpha-olefin) product; (f) terminating the catalytic polymerization of the alpha-olefin monomer; and (g) isolating the at least one type of the poly(alpha-olefin) product.

According to another aspect of the present invention, there is provided a method for catalytic polymerization of an alpha-olefin monomer, the method comprising the steps: (a) providing a diamine diphenolate catalyst having a general structure selected from the group consisting of:

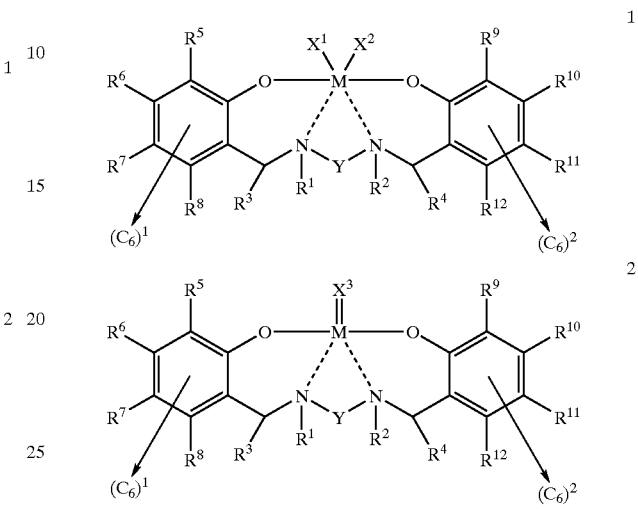

wherein each structure 1 and structure 2: each single solid line represents a covalent bond; each double solid line represents a bond having varying degrees of covalency; each dashed line represents a bond having a varying degree of covalency and a varying degree of coordination; the M is a metal atom covalently bonded to each O oxygen atom, and bonded with varying degrees of covalency and coordination to each N nitrogen atom; the $X^1$ and the $X^2$ are each a univalent anionic ligand covalently bonded to the metal atom; the $X^3$ is a single anionic ligand covalently bonded to the metal atom; the $R^1$ and the $R^2$ are each a univalent radical covalently bonded to a different one of the N nitrogen atoms; the $R^3$ is a univalent radical covalently bonded to the C carbon atom of the —$CHR^3$— of the $(C_6)^1$—$CHR^3$—N— bridging unit; the $R^4$ is a univalent radical covalently bonded to the C carbon atom of the —$CHR^4$— of the —N—$CHR^4$—$(C_6)^2$ bridging unit; each of the $R^5$ through $R^8$ is a univalent radical covalently bonded to a different one of the C carbon atoms of the $(C_6)^1$ first aromatic group; each of the $R^9$ through $R^{12}$ is a univalent radical covalently bonded to a different one of the C carbon atoms of the $(C_6)^2$ second aromatic group; and the Y is a divalent radical covalently bonded to and bridging between both of the N nitrogen atoms; (b) preparing a first chemical entity featuring a particular form of the catalyst of Step (a); (c) forming a catalytic polymerization reaction system for the catalytic polymerization of the alpha-olefin monomer by mixing the first chemical entity featuring the catalyst with the alpha-olefin monomer to be polymerized, whereby the catalyst effects the catalytic polymerization of the alpha-olefin monomer for producing at least one type of poly(alpha-olefin) product; (d) terminating the catalytic polymerization of the alpha-olefin monomer; and (e) isolating the at least one type of the poly(alpha-olefin) product.

According to another aspect of the present invention, there is provided a method for isotactic and living catalytic polymerization of 1-hexene monomer for forming isotactic poly(1-hexene) product, the method comprising the steps: (a) providing diamine diphenolate pre-catalyst [{N,N'-bis(3, 5-di-tert-butyl-2hydroxophenylmethyl)-N,N'-dimethylethylenediamine}zirconium dibenzyl]; (b) preparing a first chemical entity featuring the diamine diphenolate pre-catalyst of Step (a); (c) providing boron Lewis acid co-catalyst [B(C$_6$F$_5$)$_3$] suitable for activating the pre-catalyst of Step (a); (d) preparing a second chemical entity featuring the boron Lewis acid co-catalyst of Step (c); (e) forming an isotactic and living catalytic polymerization reaction system for the isotactic and living catalytic polymerization of the 1-hexene monomer by mixing the first chemical entity featuring the pre-catalyst with the second chemical entity featuring the co-catalyst with the 1-hexene monomer to be polymerized, whereby the co-catalyst activates the pre-catalyst for becoming a catalyst effecting the isotactic and living catalytic polymerization of the 1-hexene monomer for producing the isotactic poly(1-hexene) product; (f) terminating the catalytic polymerization of the 1-hexene monomer; and (g) isolating the isotactic poly(1-hexene) product.

The present invention introduces several benefits to the field of catalytic polymerization of alpha-olefin monomers, which, until now have been unattainable. For example, particular forms of the diamine diphenolate pre-catalyst of the present invention, when activated by a co-catalyst under mild reaction conditions, enable achieving isotactic (isospecific) polymerization of a variety of alpha-olefin monomers, such as polymerization of long chain alpha-olefin monomers, for example, 1-hexene or 1-octene, for forming a variety of poly(alpha-olefin) products such as poly(1-hexene) or poly(1-octene), having high molecular weight and low molecular weight distribution. Moreover, such catalytic systems can additionally be characterized as living. Furthermore, such isotactic and living catalytic polymerization systems can be implemented at practical commercial reaction conditions, including, in particular, operating at room temperature.

The diamine diphenolate pre-catalyst of the present invention is relatively stable under commercially applicable conditions for polymerization of alpha-olefin monomers. Moreover, the pre-catalyst, and related forms of the pre-catalyst, of the present invention are relatively simple to synthesize, primarily due to simple syntheses of the corresponding diamine di(2-hydroxyarylmethyl) ligand precursors, from a variety of commercially available inexpensive starting materials, compared to syntheses of metallocene type pre-catalysts.

BRIEF DESCRIPTION OF THE DRAWINGS

The invention is herein described, by way of example only, with reference to the accompanying drawings, wherein:

FIG. 4 is an illustration of the $^{13}$C NMR spectrum of the atactic poly(1-hexene) obtained from catalytic polymerization of 1-hexene monomer using dialkyl diamine diphenolate pre-catalyst [{N,N'-bis(3,5-dimethyl-2-hydroxophenylmethyl)-N,N'-dimethylethylenediamine}zirconium dibenzyl] 17.

DESCRIPTION OF THE PREFERRED EMBODIMENTS

Figure 1:
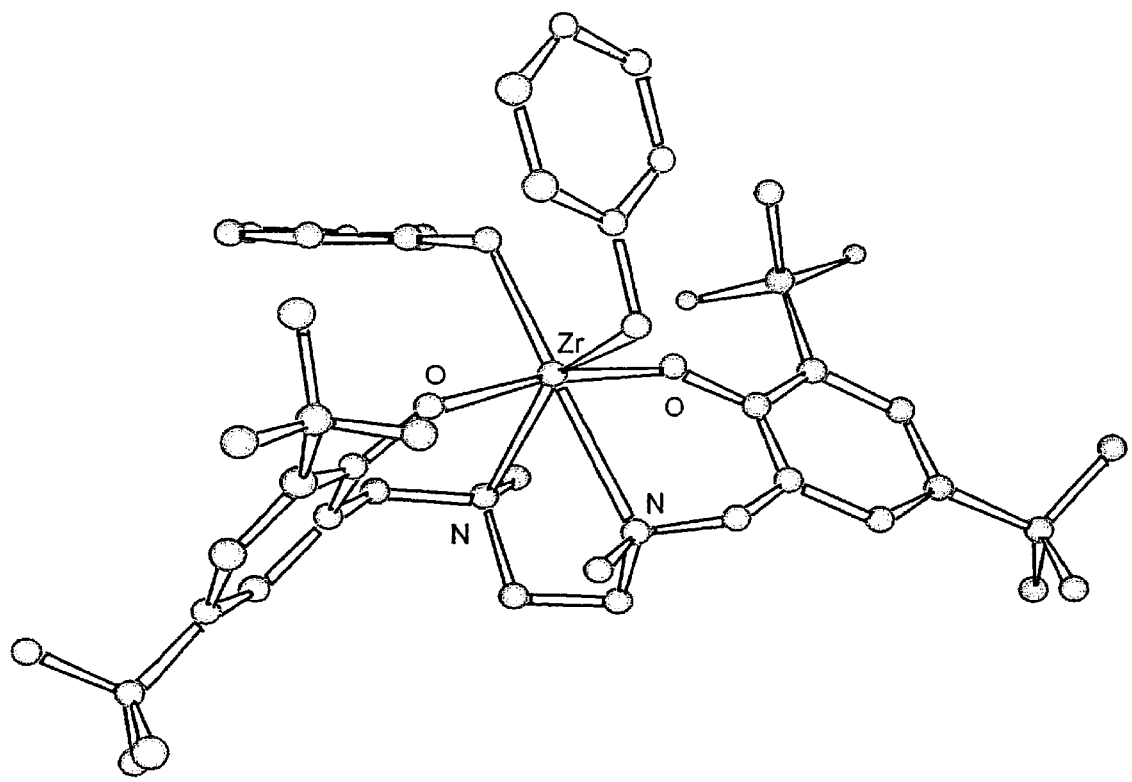
FIG. 1 is an illustration of the X-ray structure of six coordinate dialkyl diamine diphenolate pre-catalyst [{N,N'-bis(3,5-di-tert-butyl-2-hydroxophenylmethyl)-N,N'-dimethylethylenediamine}zirconium dibenzyl] 16.

The present invention relates to catalytic polymerization, in general, and, tactic catalytic polymerization, in particular, of alpha-olefin monomers using an active non-metallocene pre-catalyst featuring a diamine diphenolate complex, and a corresponding method using the disclosed pre-catalyst. The diamine diphenolate pre-catalyst of the present invention, when activated by a co-catalyst under mild reaction conditions, is active for isotactic (isospecific) and living polymerization of a variety of alpha-olefin monomers. The diamine diphenolate pre-catalyst polymerizes long chain alpha-olefin monomers such as 1-hexene or 1-octene, for forming a variety of poly(alpha-olefin) products such as poly(1-hexene) or poly(1-octene), respectively, having classifiable extent or degree of tacticity, high molecular weight and low molecular weight distribution. The diamine diphenolate pre-catalyst is relatively stable under commercially applicable conditions for polymerization of alpha-olefin monomers. Moreover, this pre-catalyst is relatively simple to synthesize, and is more available compared to currently used metallocene type pre-catalysts.

It is to be understood that the invention is not limited in its application with respect to details of exemplary preferred embodiments of chemical structures, formulas, and methods set forth in the following description, drawings, or examples. The invention is capable of other embodiments or of being practiced or carried out in various ways. Also, it is to be understood that phraseology and terminology employed herein are for the purpose of description and should not be regarded as limiting.

The diamine diphenolate pre-catalyst, and corresponding method for using this pre-catalyst for catalytic polymerization of alpha-olefin monomers, of the present invention are herein disclosed for the first time, and are not obvious nor anticipated from the ultra-high activity non-metallocene pre-catalyst featuring an amine diphenolate complex, and corresponding method for using this pre-catalyst for catalytic polymerization of alpha-olefin monomers, as disclosed in U.S. patent application Ser. No. 09/394,280, filed Sep. 20, 1999, by Kol et al. Moreover, the diamine diphenolate pre-catalyst of the present invention is not obvious nor anticipated from any of the amine diphenolate ligand precursors previously disclosed in U.S. patent application Ser. No. 09/394,280. Furthermore, diamine diphenolate ligand precursors used for synthesizing the pre-catalyst of the present invention are either new, or, are known from prior art, but are synthesized by new methods, and are not synthesized by using any of the amine diphenolate ligand precursors previously disclosed in U.S. patent application Ser. No. 09/394,280.

General structures and formulas of the diamine diphenolate pre-catalyst. The preferred embodiment of the diamine diphenolate pre-catalyst of the present invention is either general structure 1 or general structure 2:

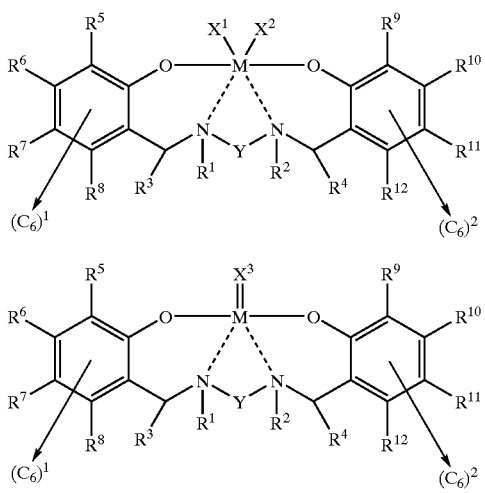

wherein a single solid line represents a covalent bond, a double solid line represents a bond having varying degrees of covalency, and a dashed line represents a coordinative bond between the indicated atoms; M is a metal atom covalently bonded to each oxygen atom, O, and, coordinately bonded to each nitrogen atom, N, as shown in structures 1 and 2 by the dashed line between the metal atom, M, and each nitrogen atom, N, where M features a transition metal atom composition, preferably, but not limited to, a single transition metal atom selected from the group consisting of zirconium, hafnium, titanium, and a lanthanide; $X^1$ and $X^2$ (structure 1) are each a univalent anionic ligand covalently bonded to the metal atom, M, such as a halide, a hydride, a saturated or unsaturated hydrocarbyl, an alkoxide, an aryloxide, a dialkylamide, or an arylamide; $X^3$ (structure 2) is a single univalent or a divalent anionic ligand covalently bonded to the metal atom, M, by either a single bond or a double bond, such as a cyclometallated hydrocarbyl, or a radical such as an alkyl or an alkylidene; $R^1$ and $R^2$ are each a univalent radical covalently bonded to a different one of the two nitrogen atoms, N, such as a hydrogen, hydrocarbyl, or any other univalent radical like a trimethylsilyl; $R^3$ is a univalent radical covalently bonded to the carbon atom of the —$CHR^3$— of the $(C_6)^1$—$CHR^3$—N— bridging unit, such as a hydrogen, a hydrocarbyl, or any other univalent radical like a benzyl; $R^4$ is a univalent radical covalently bonded to the carbon atom of the —$CHR^4$— of the —N—$CHR^4$—$(C_6)^2$ bridging unit, such as a hydrogen, a hydrocarbyl, or any other univalent radical like a benzyl; $R^5$ through $R^8$ are each a univalent radical covalently bonded to a different carbon atom in the first aromatic group, $(C_6)^1$, such as a hydrogen, a hydrocarbyl, or any other univalent radical like an alkoxide; $R^9$ through $R^{12}$ are each a univalent radical covalently bonded to a different carbon atom in the second aromatic group, $(C_6)^2$, such as a hydrogen, a hydrocarbyl, or any other univalent radical like an alkoxide; and, Y is a divalent radical covalently bonded to and bridging between the two nitrogen atoms, N, such as a dihydrocarbyl or any other divalent radical like a cycloalkane-diyl.

General formulas corresponding to general structures 1 and 2 of the diamine diphenolate pre-catalyst of the present invention are as follows: $[\{OR^5R^6R^7R^8(C_6)^1(CHR^3)NR^1YNR^2(CHR^4)(C_6)^2R^9R^{10}R^{11}R^{12}O\}MX^1X^2]$ and $[\{OR^5R^6R^7R^8(C_6)^1(CHR^3)NR^1YNR^2(CHR^4)(C_6)^2R^9R^{10}R^{11}R^{12}O\}MX^3]$, respectively.

Corresponding to previously illustrated and described general structures 1 and 2 of the pre-catalyst of the present invention, here, M is a metal atom covalently bonded to each oxygen atom, O, and, coordinatively bonded to each nitrogen atom, N, as shown in general structures 1 and 2 by the dashed line between the metal atom, M, and each nitrogen atom, N, where M features a transition metal atom composition, preferably, but not limited to, a single transition metal atom selected from the group consisting of zirconium, hafnium, titanium, and a lanthanide; $X^1$ and $X^2$ (structure 1) are each a univalent anionic ligand covalently bonded to the metal atom, M, such as a halide, a hydride, a saturated or unsaturated hydrocarbyl, an alkoxide, an aryloxide, an dialkylamide, or an arylamide; $X^3$ (structure 2) is a single univalent or a divalent anionic ligand covalently bonded to the metal atom, M, by either a single bond or a double bond, such as a cyclometallated hydrocarbyl, or a radical such as an alkyl or an alkylidene; $R^1$ and $R^2$ are each a univalent radical covalently bonded to a different one of the two nitrogen atoms, N, such as a hydrogen, hydrocarbyl, or any other univalent radical like a trimethylsilyl; $R^3$ is a univalent radical covalently bonded to the carbon atom of the —$CHR^3$— of the $(C_6)^1$—$CHR^3$—N— bridging unit, such as a hydrogen, a hydrocarbyl, or any other univalent radical like a benzyl; $R^4$ is a univalent radical covalently bonded to the carbon atom of the —$CHR^4$— of the —N—$CHR^4$—$(C_6)^2$ bridging unit, such as a hydrogen, a hydrocarbyl, or any other univalent radical like a benzyl; $R^5$ through $R^8$ are each a univalent radical covalently bonded to a different carbon atom in the first aromatic group, $(C_6)^1$, such as a hydrogen, a hydrocarbyl, or any other univalent radical like an alkoxide; $R^9$ through $R^{12}$ are each a univalent radical covalently bonded to a different carbon atom in the second aromatic group, $(C_6)^2$, such as a hydrogen, a hydrocarbyl, or any other univalent radical like an alkoxide; and, Y is a divalent radical covalently bonded to and bridging between the two nitrogen atoms, N, such as a dihydrocarbyl or any other divalent radical like a cycloalkane-diyl.

Synthesis of diamine di(2-hydroxyarylmethyl), general ligand precursor. Syntheses of different, but related, particular forms of the general ligand precursor, diamine di(2-hydroxyarylmethyl) 6, are described below, which are then used for synthesizing different, but related, particular forms of the diamine diphenolate pre-catalyst of the present invention, consistent with structures 1 and 2, and corresponding formulas thereof. Diamine 3, selected from the group consisting of an N,N'-di-primary amine, an N,N'-di-secondary amine, and an N-primary-N'-secondary diamine, reacts with aldehydes 4A and 4B, and substituted phenols 5A and 5B, by a modified Mannich reaction under variable reaction conditions, in variable solvents such as methanol and ethanol, to give different particular forms of general ligand precursor 6.

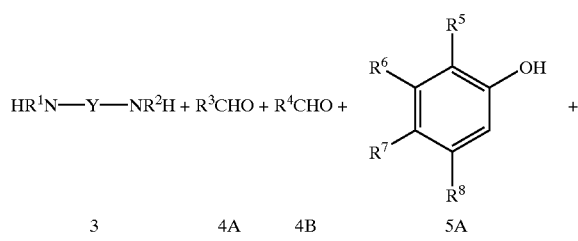

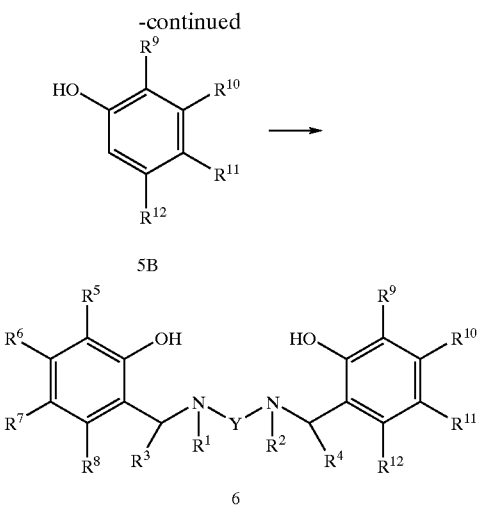

6

The structure of diamine di(2-hydroxyarylmethyl) general ligand precursor 6 features two hydroxyaryl rings, wherein the hydroxyaryl rings include a variety of substituents $R^5$ through $R^{12}$. Substituents $R^5$ through $R^8$ are each a univalent radical covalently bonded to the first hydroxyaryl ring, such as a hydrogen, a hydrocarbyl, or any other univalent radical like an alkoxide, and substituents $R^9$ through $R^{12}$ are each a univalent radical covalently bonded to the second hydroxyaryl ring, such as a hydrogen, hydrocarbyl, or any other univalent radical like an alkoxide.

The two hydroxyaryl rings are bridged by a bridging group —$CHR^3$—$NR_1$—Y—$NR^2$—$CHR^4$—, wherein as described above, $R^1$ and $R^2$ are each a univalent radical covalently bonded to one of the two nitrogen atoms, N, such as a hydrogen, hydrocarbyl, or any other univalent radical like an alkoxide; $R^3$ is a univalent radical covalently bonded to the carbon atom of the —$CHR^3$— of the $(C_6)^1$—$CHR^3$—N bridging unit, such as a hydrogen, a hydrocarbyl, or any other univalent radical like a benzyl; $R^4$ is a univalent radical covalently bonded to the carbon atom of the —$CHR^4$— of the N—$CHR^4$—$(C_6)^2$ bridging unit, such as a hydrogen, a hydrocarbyl, or any other univalent radical like a benzyl; and, Y is a divalent radical covalently bonded to and bridging between the two nitrogen atoms, N, such as a dihydrocarbyl or any other divalent radical like a cycloalkane-diyl.

Syntheses of eight exemplary, or particular, forms of diamine di(2-hydroxyarylmethyl) general ligand precursor 6 of the present invention are described herein. The first six exemplary, or particular, forms of diamine di(2-hydroxyarylmethyl) general ligand precursor 6, accordingly, particular ligand precursors 7, 8, 9, 10, 11, and 12, and their respective syntheses, are disclosed herein for the first time. The last two exemplary, or particular, forms of diamine di(2-hydroxyarylmethyl) general ligand precursor 6, accordingly, particular ligand precursors 13 and 14, are known from prior art, but their respective syntheses are disclosed herein for the first time.

Synthesis of the first exemplary ligand precursor, [N,N'-bis(3,5-di-tert-butyl-2-hydroxyphenylmethyl)-N,N'-dimethylethylenediamine] 7. The first exemplary, or particular, form of general ligand precursor 6, diamine di(2-hydroxyarylmethyl) specific ligand precursor 7, referenced hereinafter as ligand precursor [N,N'-bis(3,5-di-tert-butyl-2-hydroxyphenylmethyl)-N,N'-dimethylethylenediamine] 7 (new), is derived from reaction (not shown) of N,N'-dimethylethylenediamine as a particular form of di-secondary amine 3, with formaldehyde as a particular form of aldehydes 4A and 4B, and 2,4-di-tert-butylphenol as a particular form of substituted phenols 5A and 5B, in refluxing methanol for two hours, and isolation by filtration. Ligand precursor [N,N'-bis(3,5-di-tert-butyl-2-hydroxyphenylmethyl)-N,N'-dimethylethylenediamine] 7 is a particular form of diamine di(2-hydroxyarylmethyl) general ligand precursor 6, where $R^1$ and $R^2$ are methyl groups ($CH_3$), $R^3$, $R^4$, $R^6$, $R^8$, $R^{10}$ and $R^{12}$ are hydrogen atoms, $R^5$, $R^7$, $R^9$, and $R^{11}$ are tert-butyl groups, and Y is a divalent dihydrocarbyl radical —$CH_2CH_2$—. Further details of the synthesis and spectroscopic data are provided in Example 1 below.

Synthesis of the second exemplary ligand precursor, [N,N'-bis(3,5-dimethyl-2-hydroxyphenylmethyl)-N,N'-dimethylethylenediamine] 8. The second exemplary, or particular, form of general ligand precursor 6, diamine di(2-hydroxyarylmethyl) specific ligand precursor 8, referenced hereinafter as ligand precursor [N,N'-bis(3,5-dimethyl-2-hydroxyphenylmethyl)-N,N'-dimethylethylenediamine] 8 (new), is derived from reaction (not shown) of N,N'-dimethylethylenediamine as a particular form of di-secondary amine 3, with formaldehyde as a particular form of aldehydes 4A and 4B, and 2,4-dimethylphenol as a particular form of substituted phenols 5A and 5B, in refluxing methanol for two hours, and isolation by filtration. Ligand precursor [N,N'-bis(3,5-dimethyl-2-hydroxyphenylmethyl)-N,N'-dimethylethylenediamine] 8 is a particular form of diamine di(2-hydroxyarylmethyl) general ligand precursor 6, where $R^1$, $R^2$, $R^5$, $R^7$, $R^9$, and $R^{11}$ are methyl groups ($CH_3$), $R^3$, $R^4$, $R^6$, $R^8$, $R^{10}$, and $R^{12}$ are hydrogen atoms, and Y is a divalent dihydrocarbyl radical —$CH_2CH_2$—. Further details of the synthesis and spectroscopic data are provided in Example 2 below.

Synthesis of the third exemplary ligand precursor, [N,N'-bis(3,5-di-tert-butyl-2-hydroxyphenylmethyl)-N,N'-dibenzylethylenediamine] 9. The third exemplary, or particular, form of general ligand precursor 6, diamine di(2-hydroxyarylmethyl) specific ligand precursor 9, referenced hereinafter as ligand precursor [N,N'-bis(3,5-di-tert-butyl-2-hydroxyphenylmethyl)-N,N'-dibenzylethylenediamine] 9 (new), is derived from reaction (not shown) of N,N'-dibenzylethylenediamine as a particular form of di-secondary amine 3, with formaldehyde as a particular form of aldehydes 4A and 4B, and 2,4-di-tert-butylphenol as a particular form of substituted phenols 5A and 5B, in refluxing methanol for two hours, and isolation by filtration after precipitation using hexane solvents. Ligand precursor [N,N'-bis(3,5-di-tert-butyl-2-hydroxyphenylmethyl)-N,N'-dibenzylethylenediamine] 9 is a particular form of diamine di(2-hydroxyarylmethyl) general ligand precursor 6, where $R^1$ and $R^2$ are benzyl groups ($CH_2Ph$), $R^3$, $R^4$, $R^6$, $R^8$, $R^{10}$ and $R^{12}$ are hydrogen atoms, $R^5$, $R^7$, $R^9$ and $R^{11}$ are tert-butyl groups, and Y is a divalent dihydrocarbyl radical —$CH_2CH_2$—. Further details of the synthesis are provided in Example 3 below.

Synthesis of the fourth exemplary ligand precursor, [N,N'-bis(3,5-di-tert-butyl-2-hydroxyphenylmethyl)-N,N'-diethylethylenediamine] 10. The fourth exemplary, or particular, form of general ligand precursor 6, diamine di(2-hydroxyarylmethyl) specific ligand precursor 10, referenced hereinafter as ligand precursor [N,N'-bis(3,5-di-tert-butyl-2-hydroxyphenylmethyl)-N,N'-diethylethylenediamine] 10 (new), is derived from reaction (not shown) of N,N'-diethylethylenediamine as a particular form of di-secondary amine 3, with formaldehyde as a particular form of aldehydes 4A and 4B, and 2,4-di-tert-butylphenol as a particular form of substituted phenols 5A and 5B, in refluxing methanol for two hours, and isolation by filtration. Ligand precursor [N,N'-bis(3,5-di-tert-butyl-2-hydroxyphenylmethyl)-N,N'-diethylethylenediamine] 10 is a particular form of diamine di(2-hydroxyarylmethyl) general ligand precursor 6, where $R^1$ and $R^2$ are ethyl groups $(CH_2CH_3)$, $R^3$, $R^4$, $R^6$, $R^8$, $R^{10}$ and $R^{12}$ are hydrogen atoms, $R^5$, $R^7$, $R^9$ and $R^{11}$ are tert-butyl groups, and Y is a divalent dihydrocarbyl radical —$CH_2CH_2$—. Further details of the synthesis are provided in Example 4 below.

Synthesis of the fifth exemplary ligand precursor, [N,N'-bis(4,5-dimethyl-2-hydroxyphenylmethyl)-N,N'-dimethylethylenediamine] 11. The fifth exemplary, or particular, form of general ligand precursor 6, diamine di(2-hydroxyarylmethyl) specific ligand precursor 11, referenced hereinafter as ligand precursor [N,N'-bis(4,5-dimethyl-2-hydroxyphenylmethyl)-N,N'-dimethyl-ethylenediamine] 11 (new), is derived from reaction (not shown) of N,N'-dimethylethylenediamine as a particular form of di-secondary amine 3, with formaldehyde as a particular form of aldehydes 4A and 4B, and 3,4-dimethylphenol as a particular form of substituted phenols 5A and 5B, in refluxing methanol for two hours, and isolation by filtration. Ligand precursor [N,N'-bis(4,5-dimethyl-2-hydroxyphenylmethyl)-N,N'-dimethylethyl-enediamine] 11 is a particular form of diamine di(2-hydroxyarylmethyl) general ligand precursor 6, where $R^1$, $R^2$, R6, $R^7$, $R^{10}$ and $R^{11}$ are methyl groups $(CH_3)$, $R^3$, $R^4$, $R^5$, $R^8$, $R^9$ and $R^{12}$ are hydrogen atoms and Y is a divalent dihydrocarbyl radical —$CH_2CH_2$—. Further details of the synthesis are provided in Example 5 below.

Synthesis of the sixth exemplary ligand precursor, [N,N'-bis(3,5-di-tert-butyl-2-hydroxyphenylmethyl)-N,N'-dimethyl-1,3-propane-diamine] 12. The sixth exemplary, or particular, form of general ligand precursor 6, diamine di(2-hydroxyarylmethyl) specific ligand precursor 12, referenced hereinafter as ligand precursor [N,N'-bis(3,5-di-tert-butyl-2-hydroxyphenylmethyl)-N,N'-dimethyl-1,3-propane-diamine] 12 (new), is derived from reaction (not shown) of N,N'-dimethyl-propane-1,3-diamine as a particular form of di-secondary amine 3, with formaldehyde as a particular form of aldehydes 4A and 4B, and 2,4-di-tert-butylphenol as a particular form of substituted phenols 5A and 5B, in refluxing methanol for twelve hours, and isolation by filtration. Ligand precursor [N,N'-bis(3,5-di-tert-butyl-2-hydroxyphenylmethyl)-N,N'-dimethyl-1,3-propane-diamine] 12 is a particular form of diamine di(2-hydroxyarylmethyl) general ligand precursor 6, where $R^1$ and $R^2$ are methyl groups $(CH_3)$, $R^3$, $R^4$, $R^6$, $R^8$, $R^{10}$ and $R^{12}$ are hydrogen atoms, $R^5$, $R^7$, $R^9$ and $R^{11}$ are tert-butyl groups and Y is a divalent dihydrocarbyl radical —$CH_2CH_2CH_2$—. Further details of the synthesis are provided in Example 6 below.

Synthesis of the seventh exemplary ligand precursor, [N,N'-bis(3,5-di-tert-butyl-2-hydroxyphenylmethyl)-ethylenediamine] 13. The seventh exemplary, or particular, form of general ligand precursor 6, diamine di(2-hydroxyarylmethyl) specific ligand precursor 13, referenced hereinafter as ligand precursor [N,N'-bis(3,5-di-tert-butyl-2-hydroxyphenylmethyl)-ethylenediamine] 13 (known from prior art), is derived from reaction (not shown) of ethylenediamine as a particular form of di-primary amine 3, with formaldehyde as a particular form of aldehydes 4A and 4B, and 2,4-di-tert-butylphenol as a particular form of substituted phenols 5A and 5B, in refluxing methanol for two hours, and isolation by filtration. Ligand precursor [N,N'-bis(3,5-di-tert-butyl-2-hydroxyphenylmethyl)-ethylenediamine] 13 is a particular form of diamine di(2-hydroxyarylmethyl) general ligand precursor 6, where $R^1$, $R^2$, $R^3$, $R^4$, $R^6$, $R^8$, $R^{10}$ and $R^{12}$ are hydrogen atoms, $R^5$, $R^7$, $R^9$ and $R^{11}$ are tert-butyl groups and Y is a divalent dihydrocarbyl radical —$CH_2CH_2$—. Further details of the synthesis are provided in Example 7 below.

Synthesis of the eighth exemplary ligand precursor, [N,N'-bis(3,5-di-tert-butyl-2-hydroxyphenylmethyl)-1,3-propane-diamine] 14. The eighth exemplary, or particular, form of general ligand precursor 6, diamine di(2-hydroxyarylmethyl) specific ligand precursor 14, referenced hereinafter as ligand precursor [N,N'-bis(3,5-di-tert-butyl-2-hydroxyphenylmethyl)-1,3-propane-diamine] 14 (known from prior art), is derived from reaction (not shown) of propane-1,3-diamine, as a particular form of di-primary amine 3, with formaldehyde as a particular form of aldehydes 4A and 4B, and 2,4-di-tert-butylphenol as a particular form of substituted phenols 5A and 5B, in refluxing methanol for two hours, and isolation by filtration. Ligand precursor [N,N'-bis(3,5-di-tert-butyl-2-hydroxyphenylmethyl)-1,3-propane-diamine] 14 is a particular form of diamine di(2-hydroxyarylmethyl) general ligand precursor 6, where $R^1$, $R^2$, $R^3$, $R^4$, $R^6$, $R^8$, $R^{10}$ and $R^{12}$ are hydrogen atoms, $R^5$, $R^7$, $R^9$ and $R^{11}$ are tert-butyl groups and Y is a divalent dihydrocarbyl radical —$CH_2CH_2CH_2$—. Further details of the synthesis are provided in Example 8 below.

Synthesis of diamine diphenolate pre-catalysts. Diamine di(2-hydroxyarylmethyl) general ligand precursor 6 is targeted for binding to a metal, such as a transition metal atom composition, preferably, but not limited to, a single transition metal atom, selected from the group consisting of zirconium, hafnium, titanium, and a lanthanide, for synthesizing different particular forms of diamine diphenolate pre-catalyst 1 or 2, in accordance with the above descriptions.

Diamine di(2-hydroxyarylmethyl) general ligand precursor 6 reacts, under variable reaction conditions, with one equivalent of a transition metal complex such as zirconium tetra(benzyl), zirconium tetrakis(dimethylamide), hafnium tetra(chloride), titanium tetra(isopropoxide), or a lanthanide complex, to yield the diphenolate zirconium dibenzyl complex, the diphenolate zirconium bis(dimethylamide) complex, the diphenolate hafnium dichloride complex, the diphenolate titanium bis(isopropoxide) complex, or, the diphenolate lanthanide complex, respectively. Each complex thus formed may be used directly as a pre-catalyst for polymerization of an alpha-olefin monomer, or may be transformed into a pre-catalyst by chemical transformation, such as transformation of diamine diphenolate titanium bis(isopropoxide) into diamine diphenolate titanium dichloride using a variety of chlorinating reagents, such as trimethylsilylchloride or triethylamine hydrochloride. The diamine diphenolate titanium dichloride may be further transformed into a diamine diphenolate titanium dialkyl using a variety of alkylating reagents, such as benzyl magnesium chloride or methyl magnesium bromide.

Synthesis of four exemplary, or particular, forms of diamine diphenolate pre-catalyst 1 of the present invention are generally described here.

Synthesis of first exemplary pre-catalyst, [{N,N'-bis(3,5-di-tert-butyl-2-hydroxophenylmethyl)-N,N'-dimethylethylenediamine}zirconium dibenzyl] 16. Ligand precursor [N,N'-bis(3,5-di-tert-butyl-2-hydroxyphenyl-methyl)-N,N'-dimethylethylenediamine] 7 reacts cleanly with one equivalent of zirconium tetra(benzyl), $Zr(CH_2Ph)_4$ 15, at 65° C. yielding the hexacoordinate dialkyl diamine diphenolate pre-catalyst 16, also referenced as [{N,N'-bis(3, 5-di-tert-butyl-2-hydroxophenylmethyl)-N,N'-dimethylethylenediamine}zirconium dibenzyl] 16, quantitatively as a yellow crystalline solid.

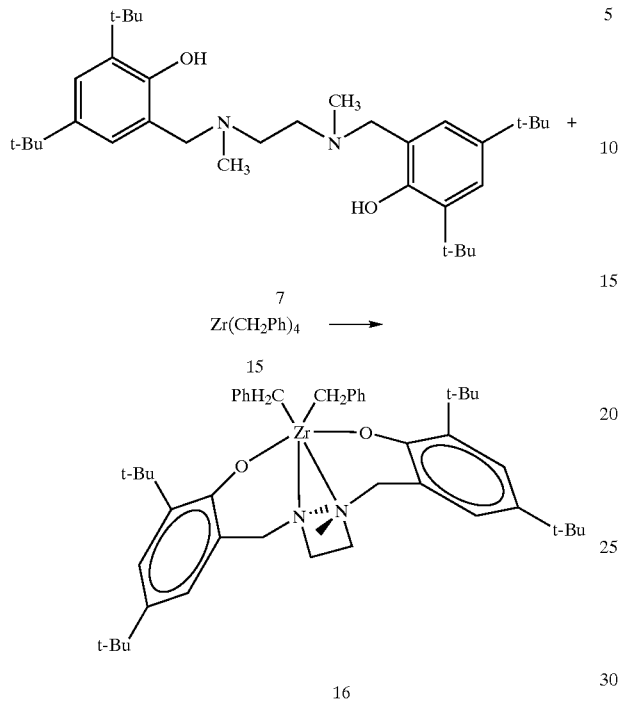

7

Zr(CH$_2$Ph)$_4$ ⟶ 15

16

Spectroscopic data of pre-catalyst 16 are consistent with a single stereoisomer featuring symmetrically related phenolate rings, symmetrically related benzyl groups, and three AX spin systems. This points to a chelate of C$_2$ symmetry on the NMR time scale. The crystallographic (X-ray) structure of pre-catalyst 16 shown in FIG. 1, supports the spectroscopic data, and indicates that the two benzyl groups are in a cis configuration. Further details of the synthesis and spectroscopic data are provided in Example 9 below.

Synthesis of second exemplary pre-catalyst, [{N,N'-bis(3,5-dimethyl-2-hydroxophenylmethyl)-N,N'-dimethyl-ethylenediamine}zirconium dibenzyl] 17. Ligand precursor [N,N'-bis(3,5-dimethyl-2-hydroxophenylmethyl)-N,N'-dimethylethylenediamine] 8 reacts cleanly with one equivalent of zirconium tetra(benzyl), Zr(CH$_2$Ph)$_4$ 15, at 65° C. yielding the hexacoordinate dialkyl diamine diphenolate pre-catalyst 17, also referenced as [{N,N'-bis(3,5-dimethyl-2-hydroxophenylmethyl)-N,N'-dimethylethylenediamine}zirconium dibenzyl] 17, quantitatively as a yellow crystalline solid.

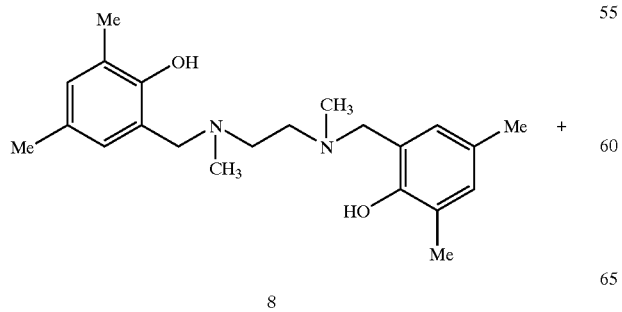

8

-continued

Zr(CH$_2$Ph)$_4$ ⟶ 15

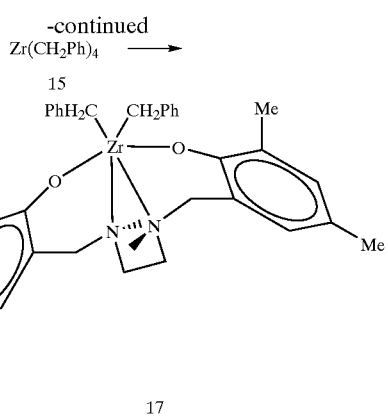

17

Spectroscopic data of pre-catalyst 17 are consistent with a single stereoisomer featuring symmetrically related phenolate rings, symmetry related benzyl groups, and three AX spin systems. This points to a chelate of C$_2$ symmetry on the NMR time scale. Further details of the synthesis and spectroscopic data are provided in Example 10 below.

Synthesis of third exemplary pre-catalyst, [{N,N'-bis(3,5-di-tert-butyl-2-hydroxophenylmethyl)-N,N'-dibenzylethylenediamine}zirconium dibenzyl] 18. Ligand precursor [N,N'-bis(3,5-di-tert-butyl-2-hydroxyphenyl-methyl)-N,N'-dibenzylethylenediamine] 9 reacts cleanly with one equivalent of zirconium tetra(benzyl), Zr(CH$_2$Ph)$_4$ 15, at 65° C. yielding the hexacoordinate dialkyl diamine diphenolate pre-catalyst 18, also referenced as [{N,N'-bis(3,5-di-tert-butyl-2-hydroxophenylmethyl)-N,N'-dibenzylethylenediamine}zirconium dibenzyl] 18, quantitatively as a yellow crystalline solid.

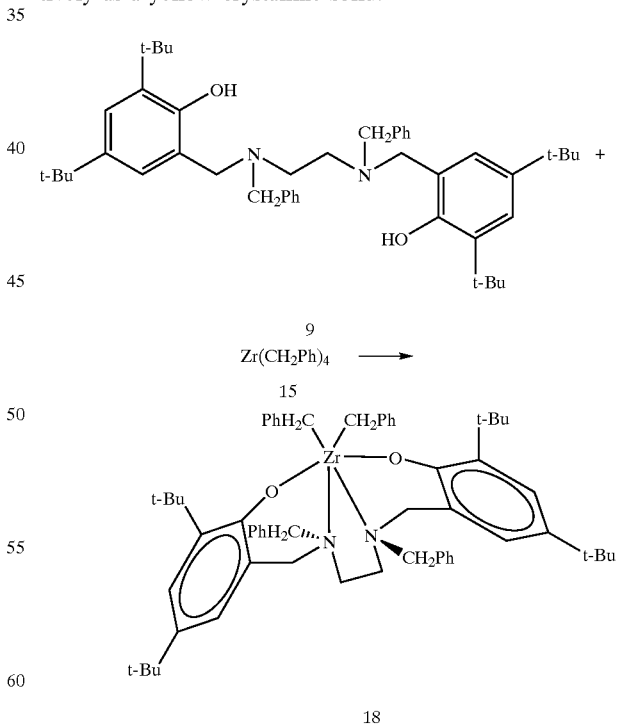

18

Spectroscopic data of pre-catalyst 18 are consistent with a single stereoisomer featuring symmetrically related phenolate rings, symmetry related benzyl groups, and three AX spin systems. This points to a chelate of C$_2$ symmetry on the NMR time scale. Further details of the synthesis are provided in Example 11 below.

Synthesis of fourth exemplary pre-catalyst, [{N,N'-bis(3,5-di-tert-butyl-2-hydroxophenylmethyl)-N,N'-diethylethylenediamine}zirconium dibenzyl] 19. Ligand precursor [N,N'-bis(3,5-di-tert-butyl-2-hydroxyphenylmethyl)-N,N'-diethylethylenediamine] 10 reacts cleanly with one equivalent of zirconium tetra(benzyl), Zr(CH$_2$Ph)$_4$ 15, at 65° C. yielding the hexacoordinate dialkyl diamine diphenolate pre-catalyst 19, also referenced as [{N,N'-bis(3,5-di-tert-butyl-2-hydroxophenylmethyl)-N,N'-diethylethylenediamine}zirconium dibenzyl] 19, quantitatively as a yellow crystalline solid.

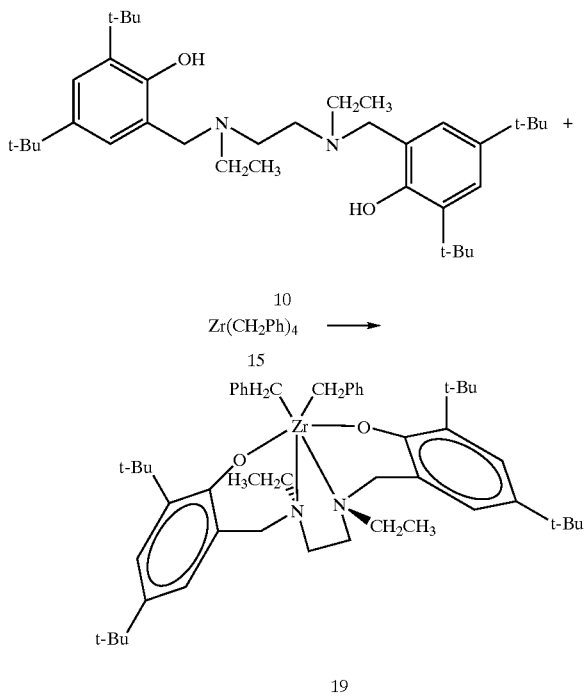

Spectroscopic data of pre-catalyst 19 are consistent with a single stereoisomer featuring symmetrically related phenolate rings, symmetry related benzyl groups, and three AX spin systems. This points to a chelate of C$_2$ symmetry on the NMR time scale. Further details of the synthesis are provided in Example 12 below.

Method for catalytic polymerization of alpha-olefin monomers. The preferred embodiment of the method for catalytic polymerization of alpha-olefin monomers, according to the present invention, is herein generally described with respect to using any particular form of diamine diphenolate pre-catalyst 1 or 2, including the four exemplary particular forms of pre-catalyst 1 as described above, namely, dialkyl diamine diphenolate pre-catalyst [{N,N'-bis(3,5-di-tert-butyl-2 hydroxophenylmethyl)-N,N'-dimethylethylenediamine}zirconium dibenzyl] 16, dialkyl diamine diphenolate pre-catalyst [{N,N'-bis(3,5-dimethyl-2-hydroxophenylmethyl)-N,N'-dimethylethylenediamine}zirconium dibenzyl] 17, dialkyl diamine diphenolate pre-catalyst [{N,N'-bis(3,5-di-tert-butyl-2-hydroxophenylmethyl)-N,N'-dibenzylethylenediamine}zirconium dibenzyl] 18, or dialkyl diamine diphenolate pre-catalyst [{N,N'-bis(3,5-di-tert-butyl-2-hydroxophenylmethyl)-N,N'-diethylethylenediamine}zirconium dibenzyl] 19, respectively.

Based on implementing the following described general method, details of two exemplary catalytic polymerization reactions, the first isotactic catalytic polymerization and the second atactic catalytic polymerization, each including the use of an exemplary alpha-olefin monomer, 1-hexene, and using particular form 16, or, particular form 17, respectively, of diamine diphenolate pre-catalyst 1 for forming poly(1-hexene) product, and related empirical data thereof, are provided in Examples 13 and 14, respectively, below.

The method for catalytic polymerization of alpha-olefin monomers, according to the present invention, described herein, is generally applicable to any type and size chemical reactor and/or chemical process. In particular, the following steps of the method of the present invention can be implemented by using a chemical reactor selected from the group consisting of a continuous flow chemical reactor, a batch chemical reactor, and a plug-flow chemical reactor, where the size of the chemical reactor is selected from the group consisting of a micro-scale laboratory chemical reactor, a product/process development scale chemical reactor, and a large scale commercial chemical reactor. Additionally, the following steps of the method of the present invention can be implemented in a chemical process selected from the group consisting of a continuous flow chemical process, a batch chemical process, a plug-flow chemical process, and a combination chemical process featuring a combination of these chemical processes, where the size of the chemical process is selected from the group consisting of a micro-scale laboratory chemical process, a product/process development scale chemical process, and a large scale commercial chemical process.

In Step (a) of the method for catalytic polymerization of an alpha-olefin monomer, there is providing a particular form of diamine diphenolate pre-catalyst 1 or 2.

In Step (b), there is preparing a first chemical entity featuring the particular form of diamine diphenolate pre-catalyst 1 or 2 of Step (a) for use in catalytic polymerization of the alpha-olefin monomer.

Preferably, there is mixing a quantity of the particular form of diamine diphenolate pre-catalyst 1 or 2 with an organic solvent. Any non-protic organic solvent may be used which is capable of suspending or dissolving, without decomposing, pre-catalyst 1 or 2. More preferably, the organic solvent is the liquid form of the alpha-olefin monomer to be polymerized, for example, an organic solvent selected from the group consisting of 1-pentene, 1-hexene, and 1-octene. Alternatively, the organic solvent is the liquid form of the alpha-olefin monomer to be polymerized, for example, an organic solvent selected from the group consisting of 1-pentene, 1-hexene, and 1-octene, mixed with at least one additional organic solvent not including the alpha-olefin monomer to be polymerized, for example, at least one additional organic solvent selected from the group consisting of pentane, heptane, toluene, methylene chloride, and chlorobenzene. Alternatively, the organic solvent is at least one organic solvent not including the alpha-olefin monomer to be polymerized, for example, at least one organic solvent selected from the group consisting of pentane, heptane, toluene, methylene chloride, and chlorobenzene.

Alternatively, there is preparing the first chemical entity featuring the particular form of diamine diphenolate pre-catalyst 1 or 2 as is, without suspending or dissolving pre-catalyst 1 or 2 in a solvent prior to subsequent Step (e), described below, of forming a catalytic polymerization reaction system for catalytic polymerization of the alpha-olefin monomer.

Ordinarily, a suitable co-catalyst is required for activating pre-catalyst 1 or 2 for effecting catalytic polymerization of the alpha-olefin monomer, however, there exist particular forms of pre-catalyst 1 or 2, for example, diphenolate lanthanide complexes, which can effect catalytic polymerization of the alpha-olefin monomer, such as 1-pentene, 1-hexene, or 1-octene, without being activated by a co-catalyst. Thus, in such catalytic polymerization systems, pre-catalyst 1 or 2 effectively functions as a 'stand-alone' catalyst, whereby there is no need for performing following Steps (c) and (d), and the method for catalytic polymerization of the alpha-olefin monomer continues with alternative Step (e), described below.

Optionally, Step (b) further includes exposing any of the above described preferred or alternative forms of the first chemical entity featuring the particular form of diamine diphenolate pre-catalyst 1 or 2, to the surface of a solid support such as silica, alumina, or magnesia, for preparing an adsorbed state of the first chemical entity of pre-catalyst 1 or 2.

In Step (c), there is providing a co-catalyst suitable for activating particular form of diamine diphenolate pre-catalyst 1 or 2, for use in catalytic polymerization of the alpha-olefin monomer. The co-catalyst is selected from the group including but not limited to, for example, a boron Lewis acid such as tris(pentafluorophenyl)boron, $B(C_6F_5)_3$, a boron salt such as N,N'-dimethyl anilinium tetrakis(pentafluoro-phenyl)borate, $[PhNH(CH_3)_2][B(C_6F_5)_4]$, and an aluminum compound such as methylaluminoxane (MAO).

In Step (d), there is preparing a second chemical entity featuring the selected co-catalyst of Step (c) for use in catalytic polymerization of the alpha-olefin monomer.

Preferably, there is mixing the selected co-catalyst, required for activating pre-catalyst 1 or 2, with an organic solvent. Any organic solvent may be used which is capable of suspending or dissolving, without decomposing, the selected co-catalyst. More preferably, the organic solvent is the liquid form of the alpha-olefin monomer to be polymerized, for example, an organic solvent selected from the group consisting of 1-pentene, 1-hexene, and 1-octene. Alternatively, the organic solvent is the liquid form of the alpha-olefin monomer to be polymerized, for example, an organic solvent selected from the group consisting of 1-pentene, 1-hexene, and 1-octene, mixed with at least one additional organic solvent not including the alpha-olefin monomer to be polymerized, for example, at least one additional organic solvent selected from the group consisting of pentane, heptane, toluene, methylene chloride, and chlorobenzene. Alternatively, the organic solvent is at least one organic solvent not including the alpha-olefin monomer to be polymerized, for example, at least one organic solvent selected from the group consisting of pentane, heptane, toluene, methylene chloride, and chlorobenzene.

Alternatively, there is preparing the second chemical entity featuring the selected co-catalyst as is, without suspending or dissolving the selected co-catalyst in a solvent prior to subsequent Step (e), described below, of forming a catalytic polymerization reaction system for catalytic polymerization of the alpha-olefin monomer.

Optionally, Step (d) further includes exposing any of the above described preferred or alternative forms of the second chemical entity featuring the selected co-catalyst, to the surface of a solid support such as silica, alumina, or magnesia, for preparing an adsorbed state of the second chemical entity of the selected co-catalyst.

With regard to above Step (b) and Step (d), the specific solvent or solvents used for suspending or dissolving diamine diphenolate pre-catalyst 1 or 2, and/or for suspending or dissolving the selected co-catalyst, depends upon the desired poly(alpha-olefin) product distribution, especially with respect to formation of different homo-polymers and co-polymers, each having a different degree of alpha-olefin monomer incorporation. Typically, when the monomer to be polymerized is liquid phase, at least one of the solvents used for suspending or dissolving diamine diphenolate pre-catalyst 1 or 2 and/or the selected co-catalyst is the alpha-olefin monomer targeted as the desired poly(alpha-olefin) product.

In Step (e), there is forming a catalytic polymerization reaction system for catalytic polymerization of the alpha-olefin monomer by mixing (i) the first chemical entity featuring the particular form of diamine diphenolate pre-catalyst 1 or 2 of Step (b), with (ii) the second chemical entity of the selected co-catalyst of Step (d), with (iii) the alpha-olefin monomer which is to be polymerized.

There are two categories, category (A) and category (B), for forming the catalytic polymerization reaction system, relating to the mixing of the first and the second chemical entities with the alpha-olefin monomer, according to the presence or absence, respectively, of the alpha-olefin monomer which is to be polymerized, in at least one of the first and second chemical entities. In addition to the presence or absence of the alpha-olefin monomer to be polymerized, in each alternative procedure of category (A) and category (B), there is mixing the first chemical entity in a state selected from the group consisting of a non-adsorbed state of the first chemical entity and an adsorbed state of the first chemical entity, with the second chemical entity in a state selected from the group consisting of a non-adsorbed state of the second chemical entity and an adsorbed state of the second chemical entity.

In category (A), wherein the alpha-olefin monomer to be polymerized is present in at least one of the chemical entities selected from the group consisting of the first chemical entity featuring pre-catalyst 1 or 2, and the second chemical entity featuring the selected co-catalyst, there is mixing the first chemical entity featuring pre-catalyst 1 or 2 with the second chemical entity featuring the selected co-catalyst.

Category (A) for forming the catalytic polymerization system includes the following five alternative procedures for mixing the first chemical entity featuring pre-catalyst 1 or 2 with the second chemical entity featuring the selected co-catalyst: (1) mixing the first chemical entity featuring pre-catalyst 1 or 2 suspended or dissolved in the alpha-olefin monomer, in a non-adsorbed state or in an adsorbed state, with the second chemical entity featuring the selected co-catalyst suspended or dissolved in the alpha-olefin monomer, in a non-adsorbed state or in an adsorbed state, (2) mixing the first chemical entity featuring pre-catalyst 1 or 2 suspended or dissolved in the alpha-olefin monomer, in a non-adsorbed state or in an adsorbed state, with the second chemical entity featuring the selected co-catalyst suspended or dissolved in an organic solvent not including the alpha-olefin monomer, in a non-adsorbed state or in an adsorbed state, (3) mixing the first chemical entity featuring pre-catalyst 1 or 2 suspended or dissolved in an organic solvent not including the alpha-olefin monomer, in a non-adsorbed state or in an adsorbed state, with the second chemical entity featuring the selected co-catalyst suspended or dissolved in the alpha-olefin monomer, in a non-adsorbed state or in an adsorbed state, (4) mixing the first chemical entity, featuring pre-catalyst 1 or 2 suspended or dissolved in the alpha-olefin monomer, in a non-adsorbed state or in an adsorbed state, with the second chemical entity featuring the selected co-catalyst as is, not suspended or dissolved in an organic solvent, in a non-adsorbed state or in an adsorbed state, and (5) mixing the first chemical entity featuring pre-catalyst 1 or 2 as is, not suspended or dissolved in an organic solvent, in a non-adsorbed state or in an adsorbed state, with the second chemical entity featuring the selected co-catalyst suspended or dissolved in the alpha-olefin monomer, in a non-adsorbed state or in an adsorbed state.

In category (B), wherein the alpha-olefin monomer to be polymerized is absent from all of the chemical entities selected from the group consisting of the first chemical entity featuring pre-catalyst 1 or 2, and the second chemical entity featuring the selected co-catalyst, there is mixing the first chemical entity featuring pre-catalyst 1 or 2 with the second chemical entity featuring the selected co-catalyst, followed by mixing with the desired or targeted alpha-olefin monomer to be polymerized.

Category (B) for forming the catalytic polymerization system includes the following four alternative procedures for mixing the first chemical entity featuring pre-catalyst 1 or 2 with the second chemical entity featuring the selected co-catalyst, followed by mixing with the alpha-olefin monomer: (1) mixing the first chemical entity featuring pre-catalyst 1 or 2 suspended or dissolved in an organic solvent not including the alpha-olefin monomer, in a non-adsorbed state or in an adsorbed state, with the second chemical entity featuring the selected co-catalyst as is, not suspended or dissolved in an organic solvent, in a non-adsorbed state or in an adsorbed state, followed by mixing with the alpha-olefin monomer, (2) mixing the first chemical entity featuring pre-catalyst 1 or 2 suspended or dissolved in an organic solvent not including the alpha-olefin monomer, in a non-adsorbed state or in an adsorbed state, with the second chemical entity featuring the selected co-catalyst suspended or dissolved in an organic solvent not including the alpha-olefin monomer, in a non-adsorbed state or in an adsorbed state, followed by mixing with the alpha-olefin monomer, (3) mixing the first chemical entity featuring pre-catalyst 1 or 2 as is, not suspended or dissolved in an organic solvent, in a non-adsorbed state or in an adsorbed state, with the second chemical entity featuring the selected co-catalyst suspended or dissolved in an organic solvent not including the alpha-olefin monomer, in a non-adsorbed state or in an adsorbed state, followed by mixing with the alpha-olefin monomer, and (4) mixing the first chemical entity featuring pre-catalyst 1 or 2 as is, not suspended or dissolved in an organic solvent, in a non-adsorbed state or in an adsorbed state, with the second chemical entity featuring the selected co-catalyst as is, not suspended or dissolved in an organic solvent, in a non-adsorbed state or in an adsorbed state, followed by mixing with the alpha-olefin monomer.

In category (B) for forming the catalytic polymerization system, according to the above described four alternative procedures, the alpha-olefin monomer is in either a liquid phase or a gas phase for mixing with the initially formed liquid phase mixture or solid phase mixture of the first chemical entity featuring pre-catalyst 1 or 2 and the second chemical entity featuring the selected co-catalyst. Accordingly, liquid phase alpha-olefin monomer is added to the initially formed liquid phase mixture or solid phase mixture of the first chemical entity featuring pre-catalyst 1 or 2 and the second chemical entity featuring the selected co-catalyst. Alternatively, gas phase alpha-olefin monomer is bubbled into and/or through the initially formed liquid phase mixture or solid phase mixture of the first chemical entity featuring pre-catalyst 1 or 2 and the second chemical entity featuring the selected co-catalyst.

According to previously described Step (b) there exist particular forms of pre-catalyst 1 or 2, for example, diphenolate lanthanide complexes, which can effect catalytic polymerization of the alpha-olefin monomer without being activated by a co-catalyst, whereby following preparation of the first chemical entity featuring the particular form of diamine diphenolate pre-catalyst 1 or 2, according to previously described Step (b), there is no need for preparing the second chemical entity featuring the selected co-catalyst, according to previously described Steps (c) and (d). Thus, in alternative Step (e) there is forming a catalytic polymerization reaction system for catalytic polymerization of the alpha-olefin monomer by mixing (i) the first chemical entity featuring the particular form of diamine diphenolate pre-catalyst 1 or 2, suspended or dissolved in liquid phase, or, as is, in liquid phase or solid phase, in a non-adsorbed state or in an adsorbed state, without including the alpha-olefin monomer, according to previously described Step (b), with (ii) the alpha-olefin monomer which is to be polymerized. Accordingly, liquid phase alpha-olefin monomer is added to the initially prepared liquid phase or solid phase of the first chemical entity featuring pre-catalyst 1 or 2 in a non-adsorbed state or in an adsorbed state. Alternatively, gas phase alpha-olefin monomer is bubbled into and/or through the initially prepared liquid phase or solid phase of the first chemical entity featuring pre-catalyst 1 or 2 in a non-adsorbed state or in an adsorbed state.

Independent of the actual order or sequence of mixing the chemical entities, completion of Step (e) results in forming the catalytic polymerization reaction system for catalytic polymerization of the alpha-olefin monomer, including (i) the first chemical entity featuring the particular form of diamine diphenolate pre-catalyst 1 or 2 of Step (b), in a non-adsorbed state or in an adsorbed state, (ii) the second chemical entity featuring the selected co-catalyst of Step (d), in a non-adsorbed state or in an adsorbed state, and (iii) the alpha-olefin monomer which is to be polymerized. Alternatively, completion of Step (e) results in forming the catalytic polymerization reaction system for catalytic polymerization of the alpha-olefin monomer, including (i) the first chemical entity featuring the particular form of diamine diphenolate pre-catalyst 1 or 2 of Step (b), in a non-adsorbed state or in an adsorbed state, and (ii) the alpha-olefin monomer which is to be polymerized.

Conditions for performing Step (a) through Step (e) are preferably room temperature, with exclusion of moisture and oxygen in order to prevent hydrolysis or oxidation of either pre-catalyst 1 or 2, or, the selected co-catalyst.

In practice, implementation of the method for catalytic polymerization of an alpha-olefin monomer, according to the present invention, preferably includes performing above described Step (e), of forming a catalytic polymerization reaction system for catalytic polymerization of the alpha-olefin monomer by mixing (i) the first chemical entity featuring the particular form of diamine diphenolate pre-catalyst 1 or 2 of Step (b), with (ii) the second chemical entity of the selected co-catalyst of Step (d), with (iii) the alpha-olefin monomer which is to be polymerized, according to any particular procedure selected from category (A) or category (B).

In principle, however, the complex chemical entity formed as a result of mixing the first chemical entity featuring pre-catalyst 1 or 2 absent of the alpha-olefin monomer, in a non-adsorbed state or in an adsorbed state, with the second chemical entity featuring the selected co-catalyst also absent of the alpha-olefin monomer, in a non-adsorbed state or in an adsorbed state, can be isolated and held as is, short term or long term, according to stability of such a complex chemical entity, without immediately exposing the complex chemical entity to an alpha-olefin monomer for forming a catalytic polymerization reaction system for catalytic polymerization of an alpha-olefin monomer. In this case, the complex chemical entity formed by activating pre-catalyst 1 or 2 with the selected co-catalyst, in the absence of alpha-olefin monomer, is effectively considered an 'active' catalyst for catalytic polymerization of an alpha-olefin monomer, such that, by separately adding an alpha-olefin monomer to the complex chemical entity, there is forming a catalytic polymerization reaction system for catalytic polymerization of the alpha-olefin monomer, in accordance with previously described category (B) of Step (e).

In Step (f), there is stirring the catalytic polymerization reaction system for a duration in the range of between about 5 seconds to about 12 hours. Starting from polymerization reaction initiation, and including duration of stirring of the reaction system, exothermic heat may be released from the reaction system, accompanied by possible color change of the reaction system. The catalytic polymerization may be conducted at different temperatures. External cooling, for example, down to about 0° C., may be used for slowing down the catalytic polymerization. Heating, for example, to reflux temperature, speeds up the reaction.

Additionally, in Step (f), there is optionally adding to the catalytic polymerization reaction system at least one other type and quantity of a chemical reagent for improving the polymerization reaction. For example, hydrogen gas is sometimes added to the catalytic polymerization reaction system for improving control of molecular weight of the resulting poly(alpha-olefin) products.

In Step (g), there is terminating the catalytic polymerization reaction by using reaction conditions selected from the group consisting of (i) adding an external quencher such as a protic solvent, (ii) completely consuming the monomer, and (iii) deactivating the catalyst previously formed according to above described Step (e), featuring a complex of the first chemical entity featuring the particular form of diamine diphenolate pre-catalyst 1 or 2 of Step (b), mixed with the second chemical entity of the selected co-catalyst of Step (d).

In Step (h), there is isolating the polymer product by the following procedure. Excess pre-catalyst 1 or 2 and/or the selected co-catalyst, may be hydrolyzed. Isolation of the polymer product from the solvent and/or remaining alpha-olefin monomer in solution depends upon the solubility of the polymer product. In the case of an insoluble polymer product, for example, polyethylene, the isolation procedure includes filtration and drying, whereas in the case of a soluble polymer product, volatile species are removed by distillation and the polymer product is then dried. Impurities, such as decomposition products of pre-catalyst 1 or 2 and/or the selected co-catalyst are typically washed away.

In Step (i), there is measuring and analyzing physicochemical properties and characteristics of the poly(alpha-olefin) products produced from the catalytic polymerization reaction system by various techniques, such as melting point, spectroscopy such as NMR, X-ray crystallography, mechanical strength such as elasticity, etc. Structural information and molecular weight information relating to polymer molecular weight distribution via the polydispersity index (PDI), are also determined.

To illustrate the great potential of the diamine diphenolate pre-catalyst 1 of the present invention for tactic catalytic polymerization of alpha-olefin monomers, highlights of catalytic polymerization reaction systems described in Examples 13 and 14, respectively, below are herein provided.

Diamine diphenolate pre-catalyst 1, in the first exemplary particular form described above, namely, hexacoordinate dialkyl diamine diphenolate pre-catalyst [{N,N'-bis(3,5-di-tert-butyl-2 hydroxophenylmethyl)-N,N'-dimethylethylenediamine}zirconium dibenzyl] 16, is activated by boron Lewis acid co-catalyst, $B(C_6F_5)_3$, in the presence of neat 1-hexene at room temperature under nitrogen gas inert atmosphere, where 1-hexene functions as both the target alpha-olefin monomer to be polymerized and as dissolution solvent for pre-catalyst 16 and for the boron co-catalyst.

Figure 2:
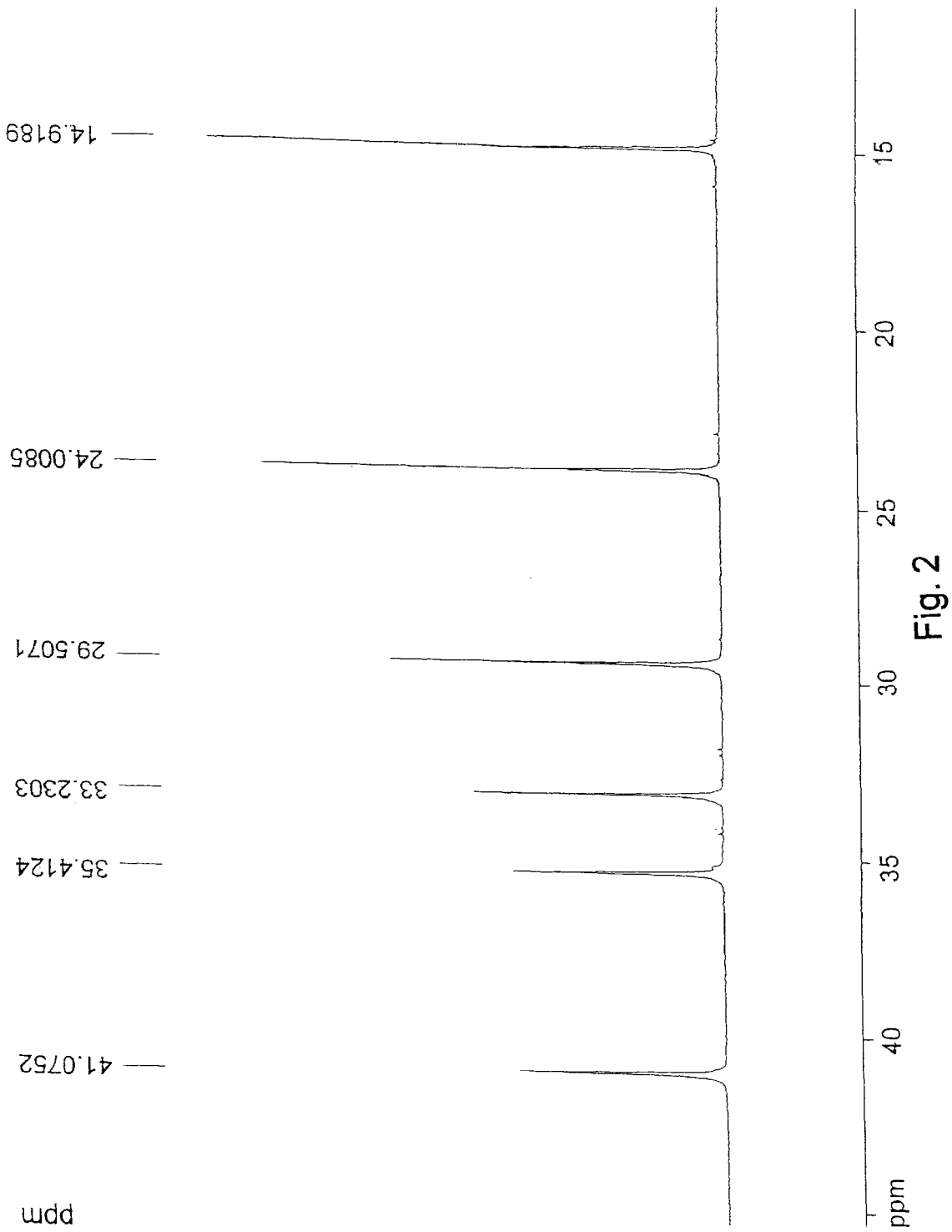
FIG. 2 is an illustration of the $^{13}$C NMR spectrum of the isotactic poly(1-hexene) product obtained from catalytic polymerization of 1-hexene monomer using dialkyl diamine diphenolate pre-catalyst [{N,N'-bis(3,5-di-tert-butyl-2-hydroxophenylmethyl)-N,N'-dimethylethylenediamine}zirconium dibenzyl] 16, in accordance with the present invention.

At these reaction conditions, there is formation of poly (1-hexene), which interestingly, is found to be highly isotactic, classifiable to an extent or degree greater than 95%, as deduced from the $^{13}C$ NMR spectrum of the resulting polymer, as shown in FIG. 2. The polymer obtained after 30 minutes has a weight average molecular weight of $M_w$=12,000 grams/mole, and a PDI of 1.15. The narrow PDI and the linear dependence of the weight average molecular weight on the consumption of the monomer shown in FIG. 3, indicate that this particular catalytic polymerization system is classifiable as living.

In another example, hexacoordinate dialkyl diamine diphenolate pre-catalyst [{N,N'-bis(3,5-dimethyl-2-hydroxophenylmethyl)-N,N'-dimethylethylenediamine}-zirconium dibenzyl] 17, is activated by boron Lewis acid co-catalyst, $B(C_6F_5)_3$, in the presence of neat 1-hexene at room temperature under nitrogen gas inert atmosphere, where again 1-hexene functions as both the target alpha-olefin monomer to be polymerized and as dissolution solvent for pre-catalyst 17, and for the boron co-catalyst. The polymer obtained in this case has a weight average molecular weight of $M_w$=23,000 grams/mole, and a PDI of 1.57. This polymer is classifiable as atactic according to its $^{13}C$ NMR spectrum shown in FIG. 4.

Catalytic activity of diamine diphenolate pre-catalyst 1 of the present invention, illustrated in part, by particular forms of six coordinate diamine diphenolate complex, pre-catalyst [{N,N'-bis(3,5-di-tert-butyl-2 hydroxophenylmethyl)-N,N'-dimethylethylenediamine}zirconium dibenzyl] 16, operating under the above described reaction conditions, is the first example of a non-metallocene catalyst which induces both isospecific and living polymerization of alpha olefin monomers.

Additional objects, advantages, and novel features of the present invention will become apparent to one ordinarily skilled in the art upon examination of the following examples, which are not intended to be limiting. Additionally, each of the various embodiments and aspects of the present invention as delineated herein above and as claimed in the claims section below finds experimental support in the following examples.

Reference is now made to the following examples, which together with the above descriptions, illustrate the invention in a non-limiting fashion. Details of the syntheses of eight different particular forms of the diamine di(2-hydroxyarylmethyl) general ligand precursor 6, are provided in Examples 1 through 8 below. Details of the syntheses and, spectroscopic and X-ray data of resulting structures of corresponding exemplary forms of the diamine diphenolate pre-catalyst 1 of the present invention are provided in Examples 9 through 12 below.

Details of catalytic polymerization of an exemplary alpha-olefin monomer, 1-hexene, using particular form 16, or, particular form 17, of the diamine diphenolate pre-catalyst 1, corresponding to isotactic catalytic polymerization, or, atactic catalytic polymerization, respectively, in accordance with the method of the present invention, for forming isotactic poly(1-hexene), or, atactic poly(1-hexene), respectively, and related empirical data thereof, are herein provided in Examples 13 and 14, respectively. Reference numbers of chemical species and structures appearing in the following examples are identical to those assigned in the above description of the preferred embodiments.

EXAMPLE 1

Synthesis of diamine di(2-hydroxyarylmethyl) Ligand Precursor [N,N'-bis(3,5-di-tert-butyl-2-hydroxyphenylmethyl)-N,N'-dimethylethylenediamine] 7

A mixture of 2,4-di-tert-butylphenol (50 mmol), N,N'-dimethylethylenediamine (25 mmol) and 37% aqueous formaldehyde (50 mmol) was stirred in refluxing methanol for 2 h. The mixture was cooled to room temperature and the solid was filtered, and washed with methanol, yielding ligand precursor 7 in 70%.

Melting point of ligand precursor 7 was 150–151° C.

Spectroscopic data of ligand precursor 7. $^1$H NMR (200 MHz, CDCl$_3$) δ10.70 (s, 2H, OH), 7.20 (d, J=2.3 Hz, 2H, Ar), 6.80 (d, J=2.3 Hz, 2H, Ar), 3.66 (s, 4H, Ar—CH$_2$—N), 2.63 (s, 4H, N—CH$_2$), 2.26 (s, 6H NCH$_3$), 1.40 (s, 18H, C(CH$_3$)$_3$), 1.27 (s, 18H, C(CH$_3$)$_3$), $^{13}$C NMR (50.4 MHz, CDCl$_3$) δ154.2, 140.6, 135.7, 123.3, 123.0, 121.0, 62.7 (Ar—CH$_2$—N), 53.8 (N—CH$_2$), 41.6 (NCH$_3$), 34.7 (C(CH$_3$)$_3$), 34.1 (C(CH$_3$)$_3$), 31.7 (C(CH$_3$)$_3$), 29.6 (C(CH$_3$)$_3$). HRMS (high resolution mass spectrometry) of ligand precursor 7: calculated, 524.43418, and observed, 524.43413.

EXAMPLE 2

Synthesis of diamine di(2-hydroxyarylmethyl) Ligand Precursor [N,N'-bis(3,5-dimethyl-2-hydroxyphenylmethyl)-N,N'-dimethylethylenediamine] 8

A mixture of 2,4-dimethylphenol (50 mmol), N,N'-dimethylethylenediamine (25 mmol) and 37% aqueous formaldehyde (50 mmol) was stirred in refluxing methanol for 2 h. The mixture was cooled to room temperature and the solid was filtered, and washed with methanol, yielding ligand precursor 8 in 50%.

Melting point of ligand precursor 8 was 120–121° C.

Spectroscopic Data of ligand precursor 8. $^1$NMR (200 MHz, CDCl$_3$) δ10.57 (s, 2H, OH), 6.87 (s, 2H, Ar), 6.62 (s, 2H, Ar), 3.63 (s, 4H, Ar—CH$_2$—N), 2.66 (s, 4H, N—CH$_2$), 2.27 (s, 6H, NCH$_3$), 2.22 (s, 6H, CH$_3$), 2.20 (s, 6H, CH$_3$). $^{13}$C NMR (50.4 MHz, CDCl$_3$) δ153.4, 130.6, 127.5, 126.6, 124.6, 120.6, 61.8 (CH$_2$), 54.1 (CH$_2$), 50.1 (CH$_3$), 20.4 (CH$_3$), 15.5 (CH$_3$).

HRMS (high resolution mass spectrometry) of ligand precursor 8: calculated, 356.24638, and observed, 356.24642.

EXAMPLE 3

Synthesis of diamine di(2-hydroxyarylmethyl) Ligand Precursor [N,N'-bis(3,5-di-tert-butyl-2-hydroxyphenylmethyl)-N,N'-dibenzylethylenediamine] 9

A mixture of 2,4-di-tert-butylphenol (50 mmol), N,N'-dibenzylethylenediamine (25 mmol) and 37% aqueous formaldehyde (50 mmol) was stirred in refluxing methanol for 2 h. The mixture was cooled to room temperature and the resulting oil was separated from the aqueous layer which was discarded, and evaporated. The product was then precipitated with hexanes, filtered and washed with hexanes, yielding ligand precursor 9 in 40%. Spectroscopic data (not shown) supports formation of ligand precursor 9.

EXAMPLE 4

Synthesis of diamine di(2-hydroxyarylmethyl) Ligand Precursor [N,N'-bis(3,5-di-tert-butyl-2-hydroxyphenylmethyl)-N,N'-diethylethylenediamine] 10

A mixture of 2,4-di-tert-butylphenol (50 mmol), N,N'-diethylethylenediamine (25 mmol) and 37% aqueous formaldehyde (50 mmol) was stirred in refluxing methanol for 2 h. The mixture was cooled to room temperature and the solid was filtered, and washed with methanol, yielding 10 in 40%. Spectroscopic data (not shown) supports formation of ligand precursor 10.

EXAMPLE 5

Synthesis of diamine di(2-hydroxyarylmethyl) Ligand Precursor [N,N'-bis(4,5-dimethyl-2-hydroxyphenylmethyl)-N,N'-dimethylethylenediamine] 11

A mixture of 3,4-dimethylphenol (50 mmol), N,N'-dimethylethylenediamine (25 mmol) and 37% aqueous formaldehyde (50 mmol) was stirred in refluxing methanol for 2 h. The mixture was cooled to room temperature and the solid was filtered, and washed with methanol, yielding 11 in 45%. Spectroscopic data (not shown) supports formation of ligand precursor 11.

EXAMPLE 6

Synthesis of diamine di(2-hydroxyarylmethyl) Ligand Precursor [N,N'-bis(3,5-di-tert-butyl-2-hydroxyphenylmethyl)-N,N'-dimethyl-1,3-propane-diamine] 12

A mixture of 2,4-di-tert-butylphenol (50 mmol), N,N'-dimethyl-1,3-propane-diamine (25 mmol) and 37% aqueous formaldehyde (50 mmol) was stirred in refluxing methanol for 12 h. The mixture was cooled to room temperature and the solid was filtered, and washed with methanol, yielding 12 in 40%. Spectroscopic data (not shown) supports formation of ligand precursor 12.

EXAMPLE 7

Synthesis of diamine di(2-hydroxyarylmethyl) Ligand Precursor [N,N'-bis(3,5-di-tert-butyl-2-hydroxyphenylmethyl)-ethylenediamine] 13

A mixture of 2,4-di-tert-butylphenol (50 mmol), ethylenediamine (25 mmol) and 37% aqueous formaldehyde (50 mmol) was stirred in refluxing methanol for 2 h. The mixture was cooled to room temperature and the solid was filtered, and washed with methanol, yielding 13 in 45%. Spectroscopic data (not shown) supports formation of ligand precursor 13.

EXAMPLE 8

Synthesis of diamine di(2-hydroxyarylmethyl) Ligand Precursor [N,N'-bis(3,5-di-tert-butyl-2-hydroxyphenylmethyl)-1,3-propane-diamine] 14

A mixture of 2,4-di-tert-butylphenol (50 mmol), propane-1,3-diamine (25 mmol) and 37% aqueous formaldehyde (50 mmol) was stirred in refluxing methanol for 2 h. The mixture was cooled to room temperature and the solid was filtered, and washed with methanol, yielding 14 in 10%. Spectroscopic data (not shown) supports formation of ligand precursor 14.

EXAMPLE 9

Synthesis of diamine diphenolate Pre-catalyst [{N, N'-bis(3,5-di-tert-butyl-2 hydroxophenylmethyl)-N, N'-dimethylethylenediamine}zirconium dibenzyl] 16

A solution of diamine di(2-hydroxyarylmethyl) ligand precursor [N,N'-bis(3,5-di-tert-butyl-2-hydroxyphenylmethyl)-N,N'-dimethylethylenediamine] 7, as synthesized according to Example 1, (200 mg, 0.38 mmol) in toluene (10 mL) was added drop wise to a solution of tetra(benzyl)zirconium 15 (0.38 mmol) in toluene (10 mL) at room temperature under nitrogen gas inert atmosphere. The reaction mixture was then heated to 65° C. and stirred for two hours. The toluene was removed from the reaction mixture under low pressure to yield pure pre-catalyst 16, quantitatively as a yellow solid.

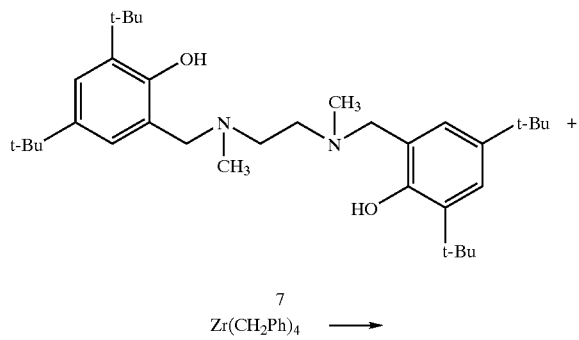

Spectroscopic Data of pre-catalyst 16. $^1$NMR (200 MHz, $C_6D_6$) δ7.62 (d, J=2.4 Hz, 2H), 7.20 (d, J=7.5 Hz, 4H), 7.04 (t, J=7.4 Hz, 4H), 6.77 (t, J=7.2 Hz, 2H), 6.76 (d, J=2.2 Hz, 2H), 3.69 (d, J=13.7 Hz, 2H, $CH_2$ AX system 1), 2.82 (d, J=10.3 2H, $CH_2$ AX system 2), 2.63 (d, J=9.3 Hz, 2H, $CH_2$ AX system 3), 2.43 (d, J=10.0 Hz, 2H, $CH_2$ AX system 2), 2.36 (d, J=13.6 Hz, 2H, $CH_2$ AX system 1), 1.82 (s, 18H, $CH_3$), 1.70 (s, 6H. $NCH_3$), 1.34 (s, 18H, $CH_3$), 0.83 (d, J=9.4 Hz, 2H, $CH_2$ AX system 3). $^{13}$C NMR (126 MHz, $C_6D_6$) δ157.7, 149.2, 141.9, 138.1, 129.3, 127.9, 126.1, 125.8, 125.0, 122.2, 69.6 ($CH_2$), 65.0 ($CH_2$), 53.5 ($CH_3$), 46.3 ($CH_2$), 36.4 ($C(CH_3)_3$), 35.1 ($C(CH_3)_3$), 32.6 ($C(CH_3)_3$), 31.1 ($C(CH_3)_3$). Spectroscopic data of pre-catalyst 16 are consistent with a single stereoisomer featuring symmetrically related phenolate rings, two symmetrically related benzyl groups, and three AX spin systems. This points to a chelate of $C_2$ symmetry on the NMR time scale.

Crystallographic (X-ray) Data for pre-catalyst $2(C_{48}H_{68}N_2O_2Zr).3(C_7H_8)$ 16: M=1868.93, monoclinic space group $P2_1/c$, a=31.0080(5), b =11.9200(3), c=29.7910 (7) Å, β=107.994(1)°, U=10472.6(4) Å$^3$, Z=4, Dc=1.185 g cm$^{-3}$μ (Mo—Koα)=0.252 mm$^{-1}$, T=115 K, Enraf-Nonius Kappa-CCD, 19001 reflections were measured (Rint= 0.000). The final refinement converged at R1=0.0493 and wR2=0.1157 for observations with [I>2σ(I)] and R1=0.0852 and wR2=0.1323 for all data.

The crystallographic (X-ray) data support the spectroscopic data, indicating a complex having a $C_2$ symmetry. The X-ray structure of pre-catalyst [(2,4-di-t-Bu—Ar—O) $CH_2$—N($CH_3$)]$_2$—($CH_2$)2—Zr($CH_2$Ph)$_2$ 16, shown in FIG. 1, indicates a structure featuring a mononuclear zirconium chelate having a slightly distorted octahedral geometry, including two coordinative bonds between Zr and each of the two nitrogen atoms. The two benzyl groups are in a cis configuration, as required for alpha-olefin polymerization catalysis.

EXAMPLE 10

Synthesis of diamine diphenolate Pre-catalyst [{N, N'-bis(3,5-dimethyl-2-hydroxophenylmethyl)-N,N'-dimethylethylenediamine}zirconium dibenzyl] 17

A solution of diamine di(2-hydroxyarylmethyl) ligand precursor [(2,4-di-Me—Ar—O)$CH_2$—N($CH_3$)]$_2$—($CH_2$)$_2$ 8, as synthesized according to Example 2, (135 mg, 0.38 mmol) in toluene (10 mL) was added drop wise to a solution of tetra(benzyl)zirconium 15 (0.38 mmol) in toluene (10 mL) at room temperature under nitrogen gas inert atmosphere. The reaction mixture was then heated to 65° C. and stirred for two hours. The toluene was removed from the reaction mixture under low pressure to yield pure pre-catalyst 17, quantitatively as a yellow solid.

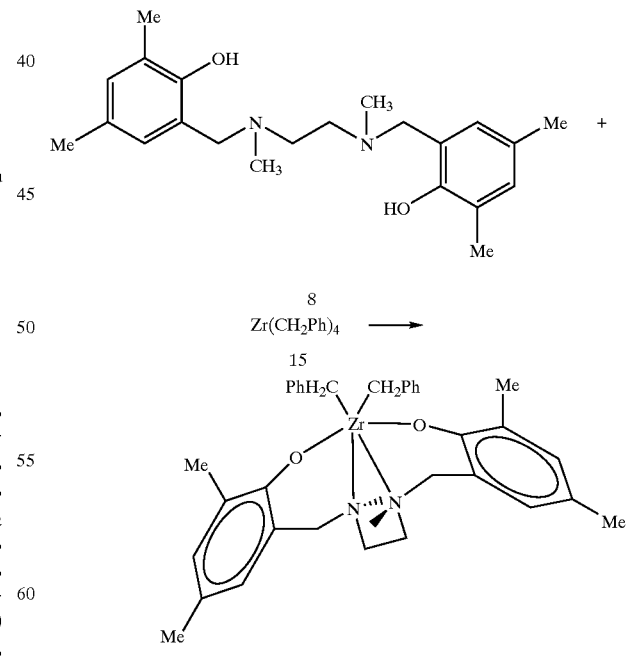

Spectroscopic Data of pre-catalyst 17. $^1$H NMR (200 MHz, $C_6D_6$) δ7.12 (m, 8H), 6.96 (d, J=1.3 Hz, 2H), 6.87 (t, J=7.0 Hz, 2H), 6.42 (d, J=1.3 Hz, 2H), 3.95 (d, J=13.6 Hz, 2H, CH$_2$ AX system 1), 2.51 (d, J=9.1 Hz, 2H, CH$_2$ AX system 2), 2.43 (s, 6H, CH$_3$), 2.34 (d, J=14.0 Hz, 2H, CH$_2$ AX system 1), 2.32 (d, J=11.5 Hz, 2H, CH$_2$ AX system 3), 2.21 (s, 6H, CH$_3$), 2.12 (d, J=10.9 Hz, 2H, CH$_2$ AX system 3), 1.73 (s, 6H, CH$_3$), 0.81 (d, J=9.0, 2H, CH$_2$ AX system 2). $^{13}$C NMR (126 MHz, C$_6$D$_6$) δ157.0, 147.7, 132.4, 129.7, 129.3, 129.1, 127.3, 127.1, 125.2, 122.9, 69.6 (CH$_2$), 64.2 (CH$_2$), 63.5 (CH$_2$), 53.6 (CH$_2$), 45.0 (CH$_3$) 21.4 (CH$_3$), 17.9 (CH$_3$).

EXAMPLE 11

Synthesis of diamine diphenolate Pre-catalyst [{N, N'-bis(3,5-di-tert-butyl-2-hydroxophenylmethyl)-N, N'-dibenzylethylenediamine}zirconium dibenzyl] 18

A solution of diamine di(2-hydroxyarylmethyl) ligand precursor [(2,4-di-t-Bu—Ar—O)CH$_2$—N(CH$_2$Ph)]$_2$—(CH$_2$)$_2$ 9, as synthesized according to Example 3, (257, mg, 0.38 mmol) in toluene (10 mL) was added drop wise to a solution of tetra(benzyl)zirconium 15 (0.38 mmol) in toluene (10 mL) at room temperature under nitrogen gas inert atmosphere. The reaction mixture was then heated to 65° C. and stirred for two hours. The toluene was removed from the reaction mixture under low pressure to yield pure pre-catalyst 18, quantitatively as a yellow solid.

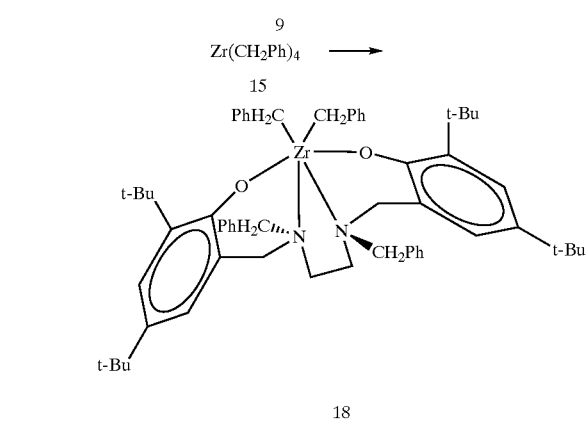

Spectroscopic data (not shown) supports formation of pre-catalyst 18.

EXAMPLE 12

Synthesis of diamine diphenolate Pre-catalyst [{N, N'-bis(3,5-di-tert-butyl-2-hydroxophenylmethyl)-N, N'-diethylethylenediamine}zirconium dibenzyl] 19

A solution of diamine di(2-hydroxyarylmethyl) ligand precursor [(2,4-di-t-Bu—Ar—O)CH$_2$—N(CH$_2$CH$_3$)]$_2$—(CH$_2$)$_2$ 10, as synthesized according to Example 4, (210 mg, 0.38 mmol) in toluene (10 mL) was added drop wise to a solution of tetra(benzyl)zirconium 15 (0.38 mmol) in toluene (10 mL) at room temperature under nitrogen gas inert atmosphere. The reaction mixture was then heated to 65° C. and stirred for two hours. The toluene was removed from the reaction mixture under low pressure to yield pure pre-catalyst 19, quantitatively as a yellow solid.

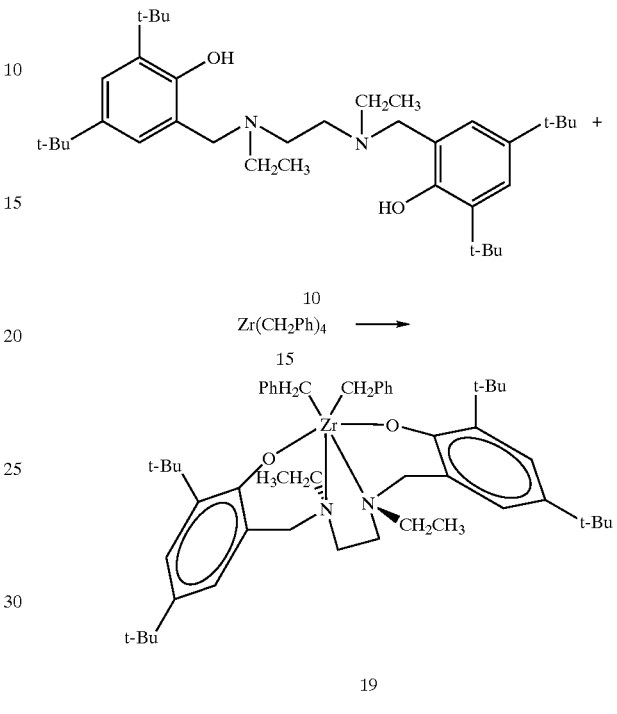

Spectroscopic data (not shown) supports formation of pre-catalyst 19.

EXAMPLE 13

Isotactic and Living Polymerization of 1-hexene Monomer Using diamine diphenolate Pre-catalyst

[{N,N'-bis(3,5-di-tert-butyl-2-hydroxophenylmethyl)-N,N'-dimethylethylenediamine}zirconium dibenzyl] 16

Data associated with this catalytic polymerization reaction system are clearly indicative of an isotactic and essentially living polymerization system. To a solution of pre-catalyst 16 (0.032 mmol) in 1-hexene (1 mL) was added a solution of co-catalyst B(C$_6$F$_5$)$_3$ (1.1 equivalent) in 1-hexene (1 mL), at room temperature under nitrogen gas inert atmosphere. The reaction mixture was stirred for 30 minutes. The remaining 1-hexene monomer reactant/solvent was removed from the reaction mixture under low pressure to yield highly isotactic, classifiable to an extent or degree greater than 95% poly(1-hexene), as a colorless oil.

Catalytic activity calculated from reaction data: (18 grams poly(1-hexene) produced)/(mmole-pre-cat. hr).

Figure 3:
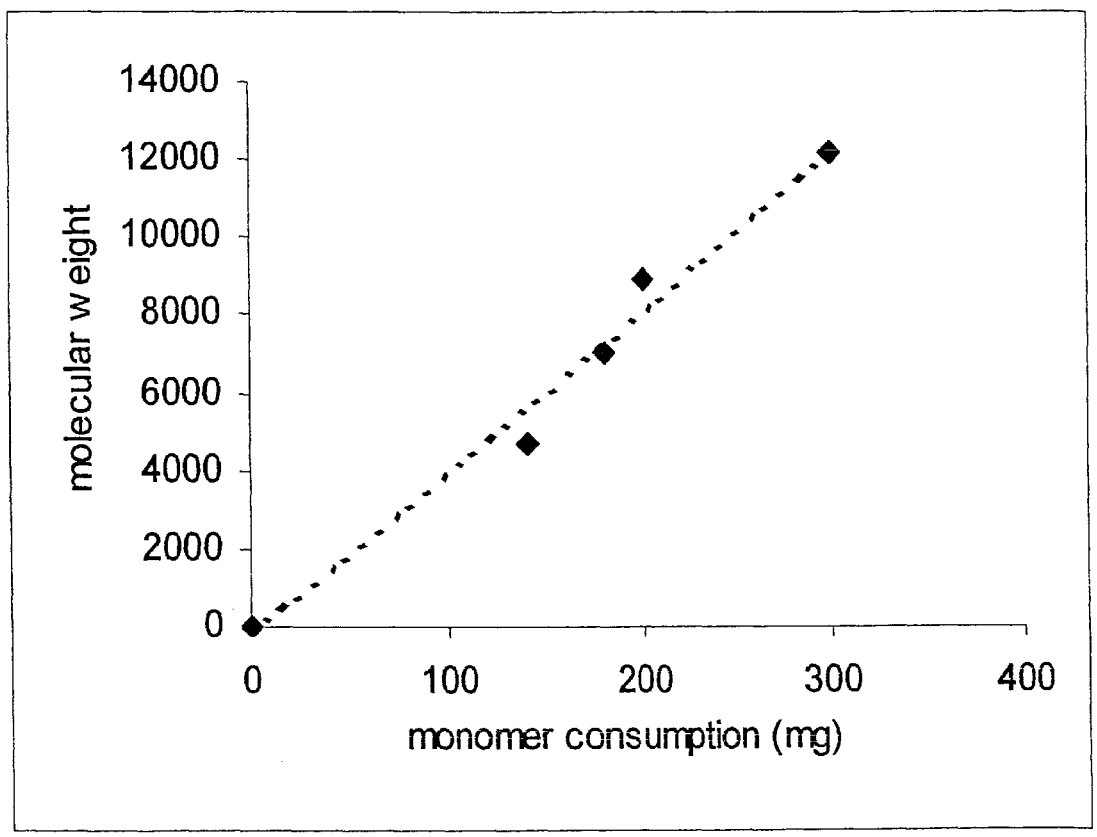
FIG. 3 is an illustration of the dependence of the weight average molecular weight M$_w$ of the poly(1-hexene) obtained from catalytic polymerization of 1-hexene monomer using dialkyl diamine diphenolate pre-catalyst [{N,N'-bis(3,5-di-tert-butyl-2-hydroxophenylmethyl)-N,N'-dimethylethylenediamine}zirconium dibenzyl] 16, on the consumption of the 1-hexene monomer.

Weight average molecular weight obtained: M$_w$=12,000 grams/mole, with a PDI of 1.15, relatively close to a PDI of 1, characteristic of a living system. Dependence of weight average molecular weight, M$_w$, on consumption of the monomer (mg) is illustrated in FIG. 3.

Spectroscopic data of the isotactic poly(1-hexene) product. 1H NMR (500 MHz, CDCl$_3$): 1.21(m, 8H, CH$_2$), 0.99 (br, 1H, CH), 0.84 (t, J=7.1 Hz, 3H, CH$_3$). $^{13}$C NMR (126

MHz, CDCl$_3$) (refer to FIG. 2): 41.21 (CH$_2$), 35.56 (CH$_2$), 33.36 (CH), 29.67 (CH$_2$), 24.17 (CH$_2$), 15.10 (CH$_3$).

EXAMPLE 14

Atactic Polymerization of 1-hexene Monomer Using diamine diphenolate Pre-catalyst [{N,N'-bis (3,5-dimethyl-2-hydroxophenylmethyl)-N,N'-dimethylethylenediamine}zirconium dibenzyl] 17

The data associated with this catalytic polymerization reaction system are clearly indicative of an atactic and essentially non-living polymerization system. To a solution of pre-catalyst 17 (0.032 mmol) in 1-hexene (1 mL) was added a solution of co-catalyst B(C$_6$F$_5$)$_3$ (1.1 equivalent) in 1-hexene (1 mL), at room temperature under nitrogen atmosphere. The reaction mixture was stirred for 30 minutes. The remaining 1-hexene monomer reactant/solvent was removed from the reaction mixture under low pressure to yield atactic poly(1-hexene), as a colorless oil.

Catalytic activity calculated from reaction data: (35 grams poly(1-hexene) produced)/(mmole-pre-cat. hr).

Weight average molecular weight obtained: M$_w$=23,000 grams/mole, with a PDI of 1.57, characteristic of an essentially non-living system.

Spectroscopic data of the atactic poly(1-hexene) product. 1H NMR (500 MHz, CDCl$_3$): 1.23 (m, 8H, CH$_2$), 1.06 (m, 1H, CH), 0.85 (t, J=6.6 Hz, 3H, CH$_3$). $^{13}$C NMR (126 MHz, CDCl$_3$) (refer to FIG. 4): 41.24 (m, CH$_2$), 35.17–34.62 (m, CH$_2$), 32.27 (CH), 29.63 (CH$_2$), 29.29 (CH$_2$), 24.19 (CH$_2$), 15.10 (CH$_3$).

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A compound having a general structure selected from the group consisting of structure 1 and structure 2:

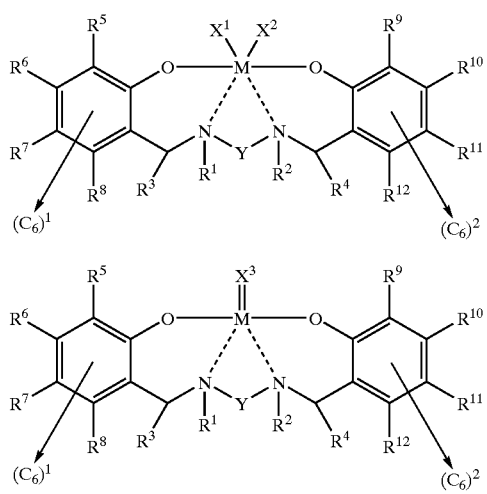

wherein each said structure 1 and said structure 2:
each said single solid line represents a covalent bond;
each said double solid line represents a bond having varying degrees of covalency;
each said dashed line represents a bond having a varying degree of covalency and a varying degree of coordination;
said M is a metal atom covalently bonded to each said O oxygen atom, and bonded with varying degrees of covalency and coordination to each said N nitrogen atom;
said X$^1$ and said X$^2$ are each a univalent anionic ligand covalently bonded to said metal atom;
said X$^3$ is a single anionic ligand covalently bonded to said metal atom;
said R$^1$ and said R$^2$ are each a univalent radical covalently bonded to a different one of said N nitrogen atoms;
said R$^3$ is a univalent radical covalently bonded to said C carbon atom of said —CHR$^3$— of said (C$_6$)$^1$—CHR$^3$—N— bridging unit;
said R$^4$ is a univalent radical covalently bonded to said C carbon atom of said —CHR$^4$— of said —N—CHR$^4$—(C$_6$)$^2$ bridging unit;
each said R$^5$ through R$^8$ is a univalent radical covalently bonded to a different one of said C carbon atoms of said (C$_6$)$^1$ first aromatic group;
each said R$^9$ through R$^{12}$ is a univalent radical covalently bonded to a different one of said C carbon atoms of said (C$_6$)$^2$ second aromatic group; and
said Y is a divalent radical covalently bonded to and bridging between both of said N nitrogen atoms.

2. The compound of claim 1, wherein said metal atom is a transition metal atom.

3. The compound of claim 2, wherein said transition metal atom is selected from the group consisting of zirconium, hafnium, titanium, and a lanthanide.

4. The compound of claim 1, wherein said X$^1$ and said X$^2$ are each selected from the group consisting of a halide, a hydride, a saturated hydrocarbyl, an unsaturated hydrocarbyl, an alkoxide, an aryloxide, a dialkylamide, and an arylamide.

5. The compound of claim 1, wherein said X$^3$ is selected from the group consisting of a single univalent anionic ligand and a single divalent anionic ligand, covalently bonded to said metal atom by a bond selected from the group consisting of a single bond and a double bond, said X$^3$ is selected from the group consisting of a cyclometallated hydrocarbyl and a radical, said radical selected from the group consisting of an alkyl radical and an alkylidene radical.

6. The compound of claim 1, wherein said R$^1$ and said R$^2$ are each selected from the group consisting of a hydrogen radical, a hydrocarbyl radical, and a trimethylsilyl radical.

7. The compound of claim 1, wherein said R$^3$ and said R$^4$ are each selected from the group consisting of a hydrogen radical, a hydrocarbyl radical, and a benzyl radical.

8. The compound of claim 1, wherein said R$^5$ through R$^8$ are each selected from the group consisting of a hydrogen radical, a hydrocarbyl radical, and an alkoxide radical.

9. The compound of claim 1, wherein said R$^9$ through R$^{12}$ are each selected from the group consisting of a hydrogen radical, a hydrocarbyl radical, and an alkoxide radical.

10. The compound of claim 1, wherein said Y is selected from the group consisting of a dihydrocarbyl radical and a cycloalkane-diyl radical.

11. The compound of claim 1, wherein a particular form of said general structure is selected from the group consisting of
[{N,N'-bis(3,5-di-tert-butyl-2-hydroxophenylmethyl)-N,N'-dimethylethylenediamine}zirconium dibenzyl],

[{N,N'-bis(3,5-dimethyl-2-hydroxophenylmethyl)-N,N'-dimethylethylenediamine}zirconium dibenzyl],
[{N,N'-bis(3,5-di-tert-butyl-2-hydroxophenylmethyl)-N,N'-dibenzylethylenediamine}zirconium dibenzyl], and
[{N,N'-bis(3,5-di-tert-butyl-2-hydroxophenylmethyl)-N,N'-diethylethylenediamine}zirconium dibenzyl].

12. The compound of claim 1, synthesized from a diamine di(2-hydroxyarylmethyl) general ligand precursor featuring two hydroxyaryl rings, wherein each of said two hydroxyaryl rings includes a variety of substituents.

13. The compound of claim 12, wherein said general ligand precursor some of said substituents of said each of said two hydroxyaryl rings are each a univalent radical covalently bonded to said each of said two hydroxyaryl rings, said substituents are selected from the group consisting of a hydrogen radical, a hydrocarbyl radical, and an alkoxide radical.

14. The compound of claim 12, wherein said general ligand precursor said two hydroxyaryl rings are bridged by a bridging group —$CHR^3$—$NR^1$—Y—$NR^2$—$CHR^4$—, wherein said $R^1$ and said $R^2$ are each a univalent radical covalently bonded to a different one of said N nitrogen atoms, said $R^1$ and said $R^2$ are each selected from the group consisting of a hydrogen radical, a hydrocarbyl radical, and a trimethylsilyl radical, said $R^3$ is a univalent radical covalently bonded to said carbon atom of said —$CHR^3$— and is selected from the group consisting of a hydrogen radical, a hydrocarbyl radical, and a benzyl radical, said $R^4$ is a univalent radical covalently bonded to said carbon atom of said —$CHR^4$— and is selected from the group consisting of a hydrogen radical, a hydrocarbyl radical, and a benzyl radical, said Y is a divalent radical covalently bonded to and bridging between said two N nitrogen atoms and is selected from the group consisting of a dihydrocarbyl radical and a cycloalkane-diyl radical.

15. The compound of claim 12, wherein said general ligand precursor is selected from the group consisting of ligand precursor
[N,N'-bis(3,5-di-tert-butyl-2-hydroxyphenylmethyl)-N,N'-dimethylethylenediamine], ligand precursor
[N,N'-bis(3,5-dimethyl-2-hydroxyphenylmethyl)-N,N'-dimethylethylenediamine], ligand precursor
[N,N'-bis(3,5-di-tert-butyl-2-hydroxyphenylmethyl)-N,N'-dibenzylethylenediamine], ligand precursor
[N,N'-bis(3,5-di-tert-butyl-2-hydroxyphenylmethyl)-N,N'-diethylethylenediamine], ligand precursor
[N,N'-bis(3,5-dimethyl-2-hydroxyphenylmethyl)-N,N'-diethylethylenediamine], ligand precursor
[N,N'-bis(3,5-di-tert-butyl-2-hydroxyphenylmethyl)-N,N'-dimethyl-1,3-propane-diamine], ligand precursor [N,N'-bis(3,5-di-tert-butyl-2-hydroxyphenylmethyl)-ethylenediamine], and
ligand precursor [N,N'-bis(3,5-di-tert-butyl-2-hydroxyphenylmethyl)-1,3-propane-diamine].

16. The compound of claim 1, used as a component for catalytic polymerization of an alpha-olefin monomer, said component is selected from the group consisting of a pre-catalyst activated by a co-catalyst for said catalytic polymerization of said alpha-olefin monomer and a catalyst for said catalytic polymerization of said alpha-olefin monomer.

17. The compound of claim 1, used as a component for tactic catalytic polymerization of an alpha-olefin monomer involving a catalytic polymerization reaction system selected from the group consisting of a non-living catalytic polymerization reaction system and a living catalytic polymerization reaction system, said component is selected from the group consisting of a pre-catalyst activated by a co-catalyst for said catalytic polymerization of said alpha-olefin monomer and a catalyst for said catalytic polymerization of said alpha-olefin monomer, for producing tactic poly(alpha-olefin) products.

18. The compound of claim 1, used as a component for tactic catalytic polymerization of an alpha-olefin monomer involving a catalytic polymerization reaction system featuring a type of chemical reactor selected from the group consisting of a continuous flow chemical reactor, a batch chemical reactor, and a plug-flow chemical reactor, where the size of the chemical reactor is selected from the group consisting of a micro-scale laboratory chemical reactor, a product/process development scale chemical reactor, and a large scale commercial chemical reactor.

19. The compound of claim 1, used as a component for tactic catalytic polymerization of an alpha-olefin monomer involving a catalytic polymerization reaction system featuring a type of chemical process selected from the group consisting of a continuous flow chemical process, a batch chemical process, and a plug-flow chemical process, where the size of the chemical process is selected from the group consisting of a micro-scale laboratory chemical process, a product/process development scale chemical process, and a large scale commercial chemical process.

20. A compound of a general formula selected from the group consisting of:
$[\{OR^5R^6R^7R^8(C_6)^1(CHR^3)NR^1YNR^2(CHR^4)(C_6)^2R^9R^{10}R^{11}R^{12}O\}MX^1X^2]$ and
$[\{OR^5R^6R^7R^8(C_6)^1(CHR^3)NR^1YNR^2(CHR^4)(C_6)^2R^9R^{10}R^{11}R^{12}O\}MX^3]$,
wherein each said general formula:
said M is a metal atom covalently bonded to each said O oxygen atom, and bonded with varying degrees of covalency and coordination to each said N nitrogen atom;
said $X^1$ and $X^2$ are each a univalent anionic ligand covalently bonded to said metal atom;
said $X^3$ is a single anionic ligand covalently bonded to said metal atom;
said $R^1$ and $R^2$ are each a univalent radical covalently bonded to a different one of said N nitrogen atoms;
said $R^3$ is a univalent radical covalently bonded to said C carbon atom of said —$CHR^3$— of said $(C_6)^1$—$CHR^3$—N— bridging unit;
said $R^4$ is a univalent radical covalently bonded to said C carbon atom of said —$CHR^4$— of said —N—$CHR^4$—$(C_6)^2$ bridging unit;
each said $R^5$ through $R^8$ is a univalent radical covalently bonded to a different one of said C carbon atoms of said $(C_6)^1$ first aromatic group;
each said $R^9$ through $R^{12}$ is a univalent radical covalently bonded to a different one of said C carbon atoms of said $(C_6)^2$ second aromatic group; and
said Y is a divalent radical covalently bonded to and bridging between both of said N nitrogen atoms.

21. The compound of claim 20, wherein said metal atom is a transition metal atom.

22. The compound of claim 21, wherein said transition metal atom is selected from the group consisting of zirconium, hafnium, titanium, and a lanthanide.

23. The compound of claim 20, wherein said $X^1$ and said $X^2$ are each selected from the group consisting of a halide, a hydride, a saturated hydrocarbyl, an unsaturated hydrocarbyl, an alkoxide, an aryloxide, a dialkylamide, and an arylamide.

24. The compound of claim 20, wherein said $X^3$ is selected from the group consisting of a single univalent anionic ligand and a single divalent anionic ligand, covalently bonded to said metal atom by a bond selected from the group consisting of a single bond and a double bond, said $X^3$ is selected from the group consisting of a cyclometallated hydrocarbyl and a radical, said radical selected from the group consisting of an alkyl radical and an alkylidene radical.

25. The compound of claim 20, wherein said $R^1$ and said $R^2$ are each selected from the group consisting of a hydrogen radical, a hydrocarbyl radical, and a trimethylsilyl radical.

26. The compound of claim 20, wherein said $R^3$ and said $R^4$ are each selected from the group consisting of a hydrogen radical, a hydrocarbyl radical, and a benzyl radical.

27. The compound of claim 20, wherein said $R^5$ through $R^8$ are each selected from the group consisting of a hydrogen radical, a hydrocarbyl radical, and an alkoxide radical.

28. The compound of claim 20, wherein said $R^9$ through $R^{12}$ are each selected from the group consisting of a hydrogen radical, a hydrocarbyl radical, and an alkoxide radical.

29. The compound of claim 20, wherein said Y is selected from the group consisting of a dihydrocarbyl radical and a cycloalkane-diyl radical.

30. The compound of claim 20, wherein a particular form of said general formula is selected from the group consisting of
[{N,N'-bis(3,5-di-tert-butyl-2-hydroxophenylmethyl)-N,N'-dimethylethylenediamine}zirconium dibenzyl],
[{N,N'-bis(3,5-dimethyl-2-hydroxophenylmethyl)-N,N'-dimethylethylenediamine}zirconium dibenzyl],
[{N,N'-bis(3,5-di-tert-butyl-2-hydroxophenylmethyl)-N,N'-dibenzylethylenediamine}zirconium dibenzyl], and
[{N,N'-bis(3,5-di-tert-butyl-2-hydroxophenylmethyl)-N,N'-diethylethylenediamine}zirconium dibenzyl].

31. The compound of claim 20, synthesized from a diamine di(2-hydroxyarylmethyl) general ligand precursor featuring two hydroxyaryl rings, wherein each of said two hydroxyaryl rings includes a variety of substituents.

32. The compound of claim 31, wherein said general ligand precursor some of said substituents of said each of said two hydroxyaryl rings are each a univalent radical covalently bonded to said each of said two hydroxyaryl rings, said substituents are selected from the group consisting of a hydrogen radical, a hydrocarbyl radical, and an alkoxide radical.

33. The compound of claim 31, wherein said general ligand precursor said two hydroxyaryl rings are bridged by a bridging group —CHR³—NR¹—Y—NR²—CHR⁴—, wherein said $R^1$ and said $R^2$ are each a univalent radical covalently bonded to a different one of said N nitrogen atoms, said $R^1$ and said $R^2$ are each selected from the group consisting of a hydrogen radical, a hydrocarbyl radical, and a trimethylsilyl radical, said $R^3$ is a univalent radical covalently bonded to said carbon atom of said —CHR³— and is selected from the group consisting of a hydrogen radical, a hydrocarbyl radical, and a benzyl radical, said $R^4$ is a univalent radical covalently bonded to said carbon atom of said —CHR⁴— and is selected from the group consisting of a hydrogen radical, a hydrocarbyl radical, and a benzyl radical, said Y is a divalent radical covalently bonded to and bridging between said two N nitrogen atoms and is selected from the group consisting of a dihydrocarbyl radical and a cycloalkane-diyl radical.

34. The compound of claim 31, wherein said general ligand precursor is selected from the group consisting of ligand precursor
[N,N'-bis(3,5-di-tert-butyl-2-hydroxyphenylmethyl)-N,N'-dimethylethylenediamine], ligand precursor
[N,N'-bis(3,5-dimethyl-2-hydroxyphenylmethyl)-N,N'-dimethylethylenediamine], ligand precursor
[N,N'-bis(3,5-di-tert-butyl-2-hydroxyphenylmethyl)-N,N'-dibenzylethylenediamine], ligand precursor
[N,N'-bis(3,5-di-tert-butyl-2-hydroxyphenylmethyl)-N,N'-diethylethylenediamine], ligand precursor
[N,N'-bis(4,5-dimethyl-2-hydroxyphenylmethyl)-N,N'-dimethylethylenediamine], ligand precursor
[N,N'-bis(3,5-di-tert-butyl-2-hydroxyphenylmethyl)-N,N'-dimethyl-1,3-propane-diamine], ligand precursor [N,N'-bis(3,5-di-tert-butyl-2-hydroxyphenylmethyl)-ethylenediamine], and
ligand precursor [N,N'-bis(3,5-di-tert-butyl-2-hydroxyphenylmethyl)-1,3-propane-diamine].

35. The compound of claim 20, used as a component for catalytic polymerization of an alpha-olefin monomer, said component is selected from the group consisting of a pre-catalyst activated by a co-catalyst for said catalytic polymerization of said alpha-olefin monomer and a catalyst for said catalytic polymerization of said alpha-olefin monomer.

36. The compound of claim 20, used as a component for tactic catalytic polymerization of an alpha-olefin monomer involving a catalytic polymerization reaction system selected from the group consisting of a non-living catalytic polymerization reaction system and a living catalytic polymerization reaction system, said component is selected from the group consisting of a pre-catalyst activated by a co-catalyst for said catalytic polymerization of said alpha-olefin monomer and a catalyst for said catalytic polymerization of said alpha-olefin monomer, for producing tactic poly(alpha-olefin) products.

37. The compound of claim 20, used as a component for tactic catalytic polymerization of an alpha-olefin monomer involving a catalytic polymerization reaction system f featuring a type of chemical reactor selected from the group consisting of a continuous flow chemical reactor, a batch chemical reactor, and a plug-flow chemical reactor, where the size of the chemical reactor is selected from the group consisting of a micro-scale laboratory chemical reactor, a product/process development scale chemical reactor, and a large scale commercial chemical reactor.

38. The compound of claim 20, used as a component for tactic catalytic polymerization of an alpha-olefin monomer involving a catalytic polymerization reaction system featuring a type of chemical process selected from the group consisting of a continuous flow chemical process, a batch chemical process, and a plug-flow chemical process, where the size of the chemical process is selected from the group consisting of a micro-scale laboratory chemical process, a product/process development scale chemical process, and a large scale commercial chemical process.

* * * * *